United States Patent
Kim et al.

(10) Patent No.: US 10,256,418 B2
(45) Date of Patent: Apr. 9, 2019

(54) ORGANOMETALLIC COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd, Yongin-si, Gyeonggi-do (KR)

(72) Inventors: Wook Kim, Suwon-si (KR); Miyoung Chae, Suwon-si (KR); Dalho Huh, Suwon-si (KR); Hyunjung Kim, Suwon-si (KR); Kangmun Lee, Suwon-si (KR); Namheon Lee, Suwon-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 287 days.

(21) Appl. No.: 14/599,792

(22) Filed: Jan. 19, 2015

(65) Prior Publication Data

US 2015/0333278 A1 Nov. 19, 2015

(30) Foreign Application Priority Data

May 16, 2014 (KR) .................. 10-2014-0059303

(51) Int. Cl.
*H01L 51/00* (2006.01)
*C07F 15/00* (2006.01)
*H01L 51/50* (2006.01)

(52) U.S. Cl.
CPC ...... *H01L 51/0085* (2013.01); *C07F 15/0033* (2013.01); *H01L 51/5012* (2013.01); *H01L 51/5016* (2013.01); *H01L 51/5068* (2013.01); *H01L 51/5084* (2013.01)

(58) Field of Classification Search
CPC ............ H01L 51/0085; H01L 51/5016; H01L 51/5012; H01L 51/5084; H01L 51/5068; C07F 15/0033
See application file for complete search history.

(56) References Cited

U.S. PATENT DOCUMENTS

| 8,247,088 B2 | 8/2012 | Ren et al. | |
| 2005/0260446 A1* | 11/2005 | Mackenzie | ........... C07F 15/002 428/690 |
| 2010/0052516 A1* | 3/2010 | Ren | ........................ C09K 11/06 313/504 |

FOREIGN PATENT DOCUMENTS

| JP | 2003-272861 | 9/2003 |
| JP | 2009511655 | 3/2009 |

OTHER PUBLICATIONS

Florian Kessler, et al., "Near-UV to red-emitting charged bis-cyclometallated iridium(III) complexes for light-emitting electrochemical cells", The Royal Society of Chemistry, Dalton Transactions, 2012, 180-191

* cited by examiner

*Primary Examiner* — Alexander C Kollias
(74) *Attorney, Agent, or Firm* — Cantor Colburn LLP

(57) ABSTRACT

An organometallic compound represented by Formula 1:

$$M(L_1)_{n1}(L_2)_{n2} \qquad \text{Formula 1}$$

wherein in Formula 1, M, $L_1$, $L_2$, n1, and n2 are defined in the detailed description.

4 Claims, 1 Drawing Sheet

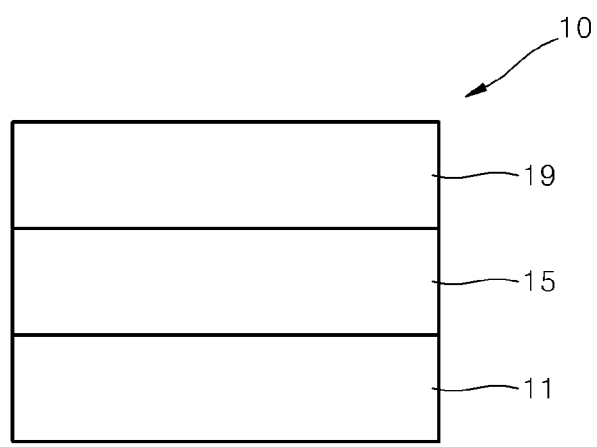

ORGANOMETALLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2014-0059303, filed on May 16, 2014, in the Korean Intellectual Property Office, and all the benefits accruing therefrom under 35 U.S.C. § 119, the content of which is incorporated herein in its entirety by reference.

BACKGROUND

1. Field

The present disclosure relates to organometallic compounds and organic light-emitting devices including the same.

2. Description of the Related Art

Organic light emitting devices (OLEDs) are self-emission devices that have wide viewing angles, high contrast ratios, and short response times. In addition, OLEDs exhibit excellent brightness, driving voltage, and response speed characteristics, and produce full-color images.

A typical organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons are recombined in the emission layer to produce excitons. These excitons change from an excited state to a ground state, thereby generating light.

Various types of organic light emitting devices are known. However, there still remains a need in OLEDs having low driving voltage, high efficiency, high brightness, and long lifespan.

SUMMARY

Provided are novel organometallic compounds and organic light-emitting devices including the same.

Additional aspects will be set forth in part in the description which follows and, in part, will be apparent from the description, or may be learned by practice of the presented embodiments.

According to an aspect, an organometallic compound is represented by Formula 1:

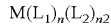    Formula 1 wherein in Formula 1,

M may be selected from Ir, Pt, Os, Ti, Zr, Hf, Eu, Tb, and Tm;

$L_1$ may be selected from ligands represented by Formula 2;

$L_2$ may be selected from a monovalent organic ligand, a divalent organic ligand, a trivalent organic ligand, and a tetravalent organic ligand, and is different from $L_1$;

n1 may be 1, 2, or 3;

n2 may be 0, 1, 2, or 4;

when n1 is two or more, ligands $L_1$ may be identical or different, and when n2 is two or more, ligands $L_2$ may be identical to different;

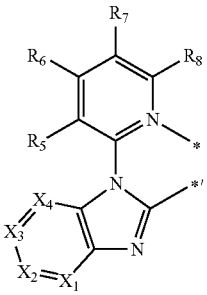    Formula 2 wherein in Formula 2, $X_1$ is N or $C(R_1)$;

$X_2$ is N or $C(R_2)$;

$X_3$ is N or $C(R_3)$; and $X_4$ is N or $C(R_4)$;

$R_1$ to $R_8$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, and —$B(Q_6)(Q_7)$, provided that each of $R_5$ to $R_8$ is not simultaneously a hydrogen;

* and *' each indicates a binding site to M in Formula 1;

at least one of substituents of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

According to another aspect, an organic light-emitting device includes:

a first electrode;

a second electrode; and an organic layer disposed between the first electrode and the second electrode, wherein the organic layer includes an emission layer, and further includes at least one organometallic compound represented by Formula 1.

The organometallic compound may be included in the emission layer, the organometallic compound included in the emission layer may act as a dopant, and the emission layer may further include a host.

BRIEF DESCRIPTION OF THE DRAWINGS

These and/or other aspects will become apparent and more readily appreciated from the following description of the embodiments, taken in conjunction with FIG. 1 which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

An organometallic compound according to an embodiment is represented by Formula 1:

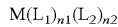   Formula 1

M in Formula 1 may be selected from iridium (Ir), platinum (Pt), osmium (Os), titanium (Ti), zirconium (Zr), hafnium (Hf), europium (Eu), terbium (Tb), and thulium (Tm).

For example, M in Formula 1 may be iridium or platinum, but is not limited thereto.

In Formula 1, $L_1$ is selected from ligands represented by Formula 2, $L_2$ is selected from a monovalent organic ligand, a divalent organic ligand, a trivalent organic ligand, and a tetravalent organic ligand, and $L_2$ is different from $L_1$.

$L_1$ and $L_2$ in Formula 2 will be described in detail later.

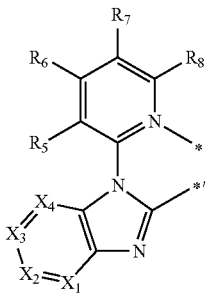

Formula 2

In Formula 1, n1 is 1, 2, or 3, and n2 is 0, 1, 2, 3, or 4.

The organometallic compound represented by Formula 1 is "neutral." That is, the organometallic compound represented by Formula 1 is not a salt consisting of the pair of a cation and an anion. Accordingly, a layer including the organometallic compound represented by Formula 1 may be formed by deposition. For example, a layer including the organometallic compound represented by Formula 1 may be effectively formed by deposition at a temperature of about 100 to about 500° C., at a vacuum degree of about $10^{-8}$ to about $10^{-3}$ torr, and at a deposition speed of about 0.01 to about 100 Angstrom per second (Å/sec). Accordingly, a device including the organometallic compound represented by Formula 1 may have improved manufacturing workability.

In Formula 2, $X_1$ may be N or $C(R_1)$, $X_2$ may be N or $C(R_2)$, $X_3$ may be N or $C(R_3)$, and $X_4$ may be N or $C(R_4)$.

For example, in Formula 2, $X_1$ may be $C(R_1)$, $X_2$ may be $C(R_2)$, $X_3$ may be $C(R_3)$, and $X_4$ may be $C(R_4)$, but they are not limited thereto.

$R_1$ to $R_8$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), provided that each of $R_5$ to $R_8$ in Formula 2 is not simultaneously a hydrogen. In other words, at least one of $R_5$ to $R_8$, which are substituents of a pyridine ring in Formula 2, is selected from substituents other than hydrogen. $Q_1$ to $Q_7$ may be understood by referring to a detailed description thereof to be provided later.

According to an embodiment, in Formula 2, $R_1$ to $R_8$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_2$-$C_{20}$ heteroaryl group, a substituted or unsubstituted monovalent non-aromatic condensed polycyclic group, a substituted or unsubstituted monovalent non-aromatic condensed heteropolycyclic group, and —Si($Q_3$)($Q_4$)($Q_5$).

In some embodiments, $R_1$ to $R_8$ in Formula 2 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and —Si($Q_{33}$)($Q_{34}$)($Q_{35}$); and —Si($Q_3$)($Q_4$)($Q_5$), wherein $Q_3$ to $Q_5$ and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group, but they are not limited thereto.

In some embodiments, $R_1$ to $R_8$ in Formula 2 may be each independently selected from a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group;

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group, each substituted with at least one selected from —F, a cyano group, a nitro group, a phenyl group, a naphthyl group, a pyridinyl group, a pyrimidinyl group, a triazinyl group, and —Si($Q_{33}$)($Q_{34}$)($Q_{35}$); and —Si($Q_3$)($Q_4$)($Q_5$), wherein $Q_3$ to $Q_5$ and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group, but they are not limited thereto.

For example, $L_1$ in Formula 1 may be selected from a ligand represented by Formula 2A below through a ligand represented by Formula 2D below, but is not limited thereto.

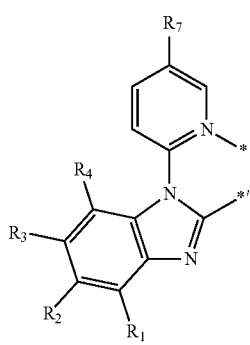

Formula 2A

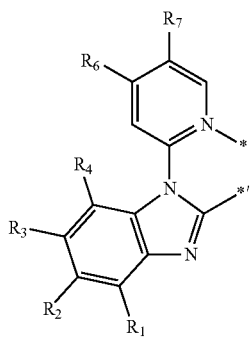

Formula 2B

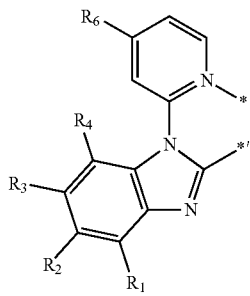

Formula 2C

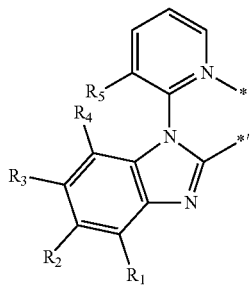

Formula 2D $R_1$ to $R_7$ in Formulae 2A to 2D may be understood by referring to the corresponding description provided herein, and $R_5$ to $R_7$ in Formulae 2A to 2D are not simultaneously a hydrogen.

* and *' in Formulae 2A to 2D are binding sites to M in Formula 1.

For example, $R_5$ to $R_7$ in Formulae 2A to 2D may be each independently selected from a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group; and a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group, each substituted with at least one selected from —F, a cyano group, a nitro group, a phenyl group, a naphthyl group, a pyridinyl group, a pyrimidinyl group, a triazinyl group, and —Si($Q_{33}$)($Q_{34}$)($Q_{35}$); and $R_1$ to $R_4$ may be each independently selected from a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, and —Si($Q_3$)($Q_4$)($Q_5$), wherein $Q_3$ to $Q_5$ and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group, but they are not limited thereto.

$L_2$ in Formula 1 may be selected from a ligand represented by Formula 3 below, a ligand represented by Formula 4 below, and a ligand represented by one of Formulae 5-1 to 5-4:

Formula 3

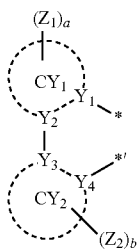

Formula 4

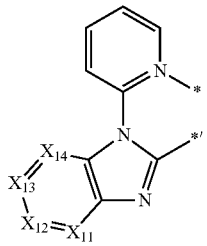

Formula 5-1

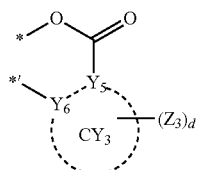

Formula 5-2

Formula 5-3

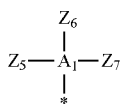

Formula 5-4

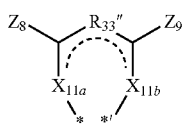

$Y_1$ to $Y_4$ in Formula 3 are each independently carbon (C) or nitrogen (N).

For example, in Formula 3, $Y_1$ may be N and $Y_4$ may be C, but they are not limited thereto.

For example, in Formula 3, $Y_2$ and $Y_3$ may be C, but they are not limited thereto.

In Formula 3, $Y_1$ and $Y_2$ may be linked to each other via a single bond or a double bond, and $Y_3$ and $Y_4$ may be linked to each other via a single bond or a double bond.

In Formula 3, $CY_1$ and $CY_2$ may be each independently a $C_5$-$C_{60}$ carbocyclic group or a $C_2$-$C_{60}$ heterocyclic group, and optionally, $CY_1$ and $CY_2$ may be linked to each other via a single bond or a first linking group.

For example, in Formula 3, $CY_1$ and $CY_2$ may be each independently a benzene, a naphthalene, a fluorene, a spirofluorene, an indene, a pyrrole, a thiophene, a furan, a imidazole, a pyrazole, a thiazole, an isothiazole, an oxazole, an isooxazole, a triazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzooxazole, an isobenzooxazole, a triazole, a tetrazole, an oxadiazole, a triazine, a dibenzofuran, a dibenzothiophene, a benzofuropyridine, or a benzothienopyridine.

According to an embodiment, in Formula 3, $CY_1$ may be a pyridine, a triazole, an imidazole, a pyrazole, a benzofuropyridine, or a benzothienopyridine, and $CY_2$ may be a benzene or a pyridine, but they are not limited thereto.

In some embodiments, in Formula 3, $CY_1$ and $CY_2$ are linked to each other via a single bond or a first linking group, and the first linking group may be represented by Formula 6 below:

$$*\text{—}(Z_{31})_{c1}\text{—}*' \qquad \text{Formula 6}$$

$Z_{31}$ in Formula 6 may be *—O—*', *—S—*', *—N($Q_{41}$)-*', *—C($Q_{42}$)($Q_{43}$)-*', *—C($Q_{44}$)=C($Q_{45}$)-*', or

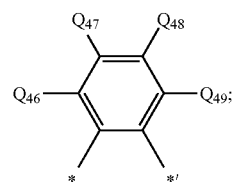

$Q_{41}$ to $Q_{49}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group; or a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group; and c1 is an integer of 1 to 10, and when c1 is 2 or more, groups $Z_{31}$ may be identical or different.

$Q_{41}$ to $Q_{49}$ may be understood by referring to a detailed description to be stated herein in connection with $Z_1$.

For example, $R_{41}$ to $R_{49}$ in Formula 6 may be each independently selected from a hydrogen atom, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a pyridinyl group, and a pyrimidinyl group; and a phenyl group, a naphthyl group, a pyridinyl group, and a pyrimidinyl group; but they are not limited thereto.

For example, in Formula 3, $CY_1$ and $CY_2$ may be linked to each other via a single bond or a first linking group, the first linking group may be represented by *—C($Q_{44}$)($Q_{44}$)$_{45}$-*' or

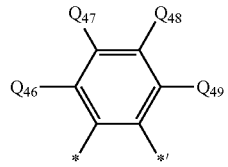

(that is, b1 in Formula 6 is 1), and $Q_{44}$ to $Q_{49}$ may be each independently a hydrogen, a $C_1$-$C_{10}$ alkyl group, or a $C_1$-$C_{10}$ alkoxy group, but they are not limited thereto.

In Formula 4, $X_{11}$ may be N or C($R_{11}$),
$X_{12}$ may be N or C($R_{12}$),
$X_{13}$ may be N or C($R_{13}$), and
$X_{14}$ may be N or C($R_{14}$).

For example, in Formula 4, $X_{11}$ may be C($R_{11}$),
$X_{12}$ may be C($R_{12}$),
$X_{13}$ may be C($R_{13}$), and
$X_{14}$ may be C($R_{14}$), but they are not limited thereto.

$Z_1$, $Z_2$, and $R_{11}$ to $R_{14}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

Examples of $Z_1$, $Z_2$, and $R_{11}$ to $R_{14}$ may be understood by referring to detailed examples of $R_1$ presented herein.

a and b in Formula 3 may be each independently an integer of 1 to 5. For example, a and b may be each independently 1 or 2, but they are not limited thereto.

* and *' in Formulae 3 and 4 are binding sites to M in Formula 1.

$Y_5$ and $Y_6$ in Formula 5-1 may be each independently carbon (C) or nitrogen (N).

$Y_5$ and $Y_6$ in Formula 5-1 may be linked to each other via a single bond or a double bond.

$CY_3$ in Formula 5-1 may be a $C_5$-$C_{60}$ carbocyclic group or a $C_2$-$C_{60}$ heterocyclic group. Examples of $CY_3$ in Formula 5-1 may be understood by referring to examples stated herein in connection with $CY_1$ and $CY_2$.

$Z_3$ to $Z_9$ in Formulae 5-1 to 5-4 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group. $Z_3$ to $Z_9$ may be understood by referring to the description provided herein in connection with $Z_1$.

$A_1$ in Formulae 5-3 may be P or As.

$X_{11a}$ and $X_{11b}$ in Formula 5-4 may be each independently N, O, N($R_{34}$), P($R_{35}$)($R_{36}$), or As($R_{37}$)($R_{38}$). $R_{34}$ to $R_{38}$ may be understood by referring to the description provided herein in connection with $Z_1$.

$R_{33}$" in Formula 5-4 may be a single bond, a double bond, a substituted or unsubstituted $C_1$-$C_5$ alkylene group, or a substituted or unsubstituted $C_2$-$C_5$ alkenylene group.

* and *' in Formulae 5-1 to 5-4 are binding sites to M in Formula 1.

In an embodiment, $L_2$ in Formula 1 may be selected from the ligand represented by Formula 3 and the ligand represented by Formula 4.

In some embodiments, $L_2$ in Formula 1 may be selected from a ligand represented by Formula 3-1 to a ligand represented by 3-142, but is not limited thereto:

Formula 3-1
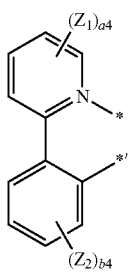
Formula 3-2
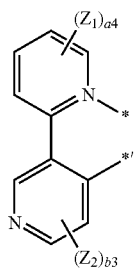
Formula 3-3
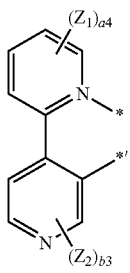
Formula 3-4
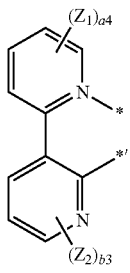
Formula 3-5
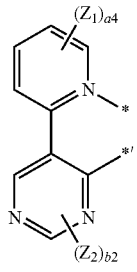
Formula 3-6
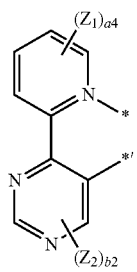
Formula 3-7
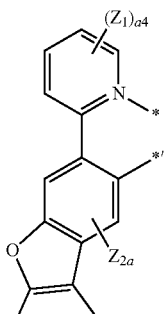
Formula 3-8
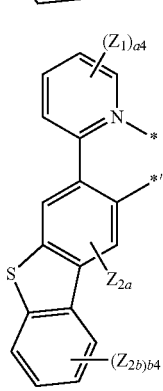
Formula 3-9
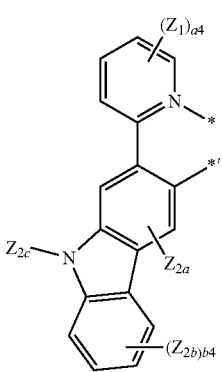
Formula 3-10
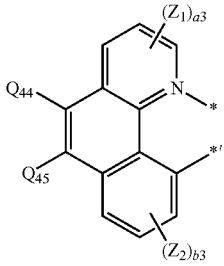
Formula 3-11
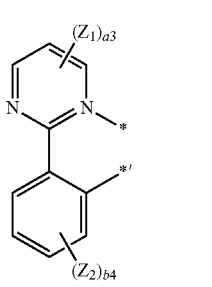

-continued

Formula 3-12

Formula 3-13

Formula 3-14

Formula 3-15

Formula 3-16

-continued

Formula 3-17

Formula 3-18

Formula 3-19

Formula 3-20

Formula 3-21

Formula 3-22
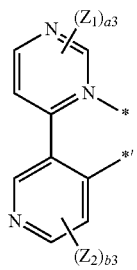
Formula 3-23
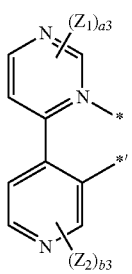
Formula 3-24
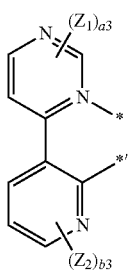
Formula 3-25
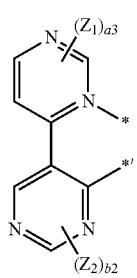
Formula 3-26
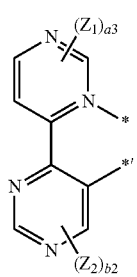
Formula 3-27
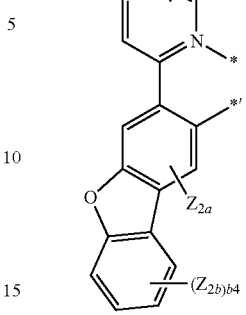
Formula 3-28
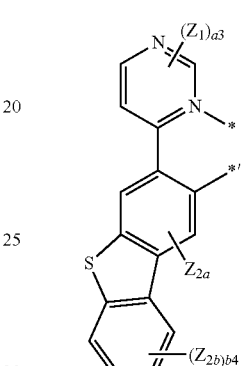
Formula 3-29
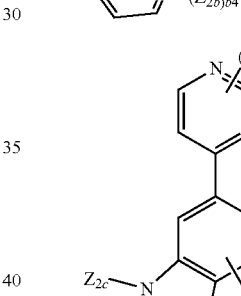
Formula 3-30
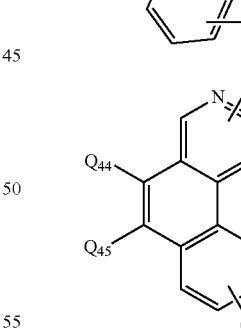
Formula 3-31
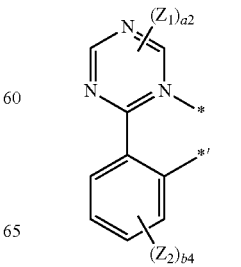

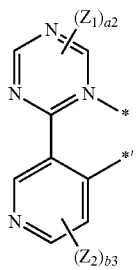
Formula 3-32
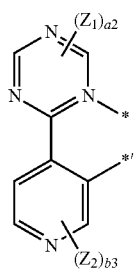
Formula 3-33
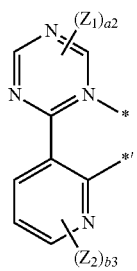
Formula 3-34
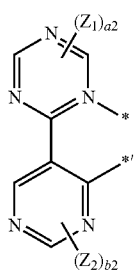
Formula 3-35
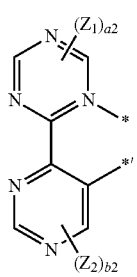
Formula 3-36
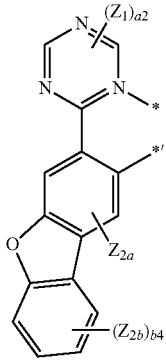
Formula 3-37
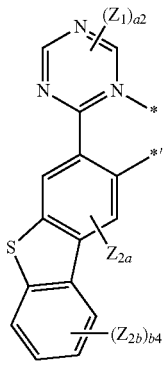
Formula 3-38
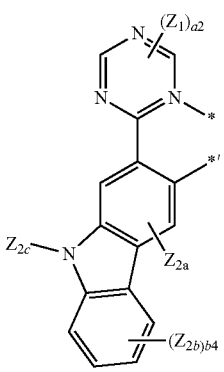
Formula 3-39
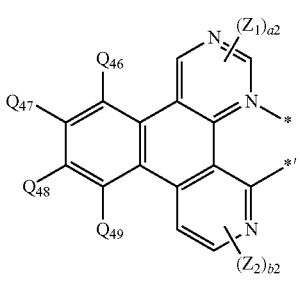
Formula 3-40
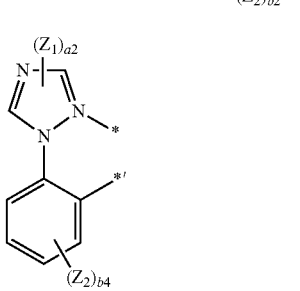
Formula 3-41

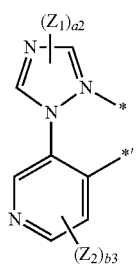
Formula 3-42
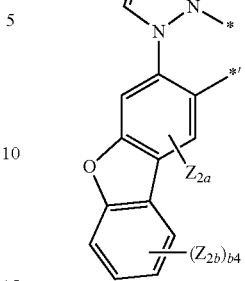
Formula 3-47
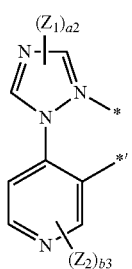
Formula 3-43
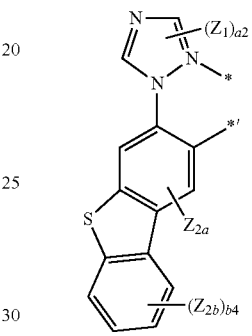
Formula 3-48
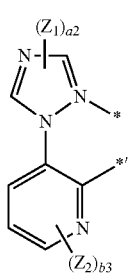
Formula 3-44
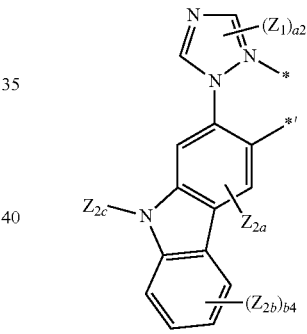
Formula 3-49
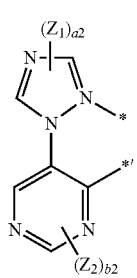
Formula 3-45
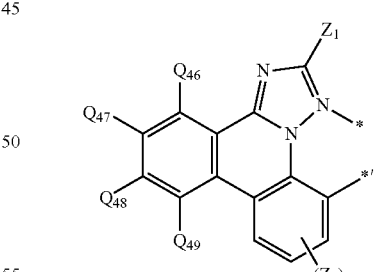
Formula 3-50
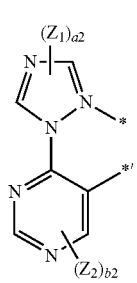
Formula 3-46
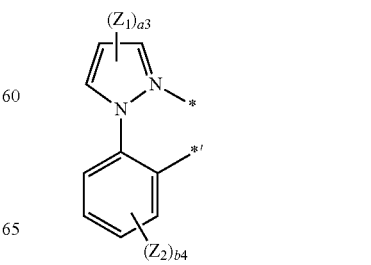
Formula 3-51

-continued
Formula 3-52
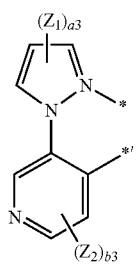
Formula 3-53
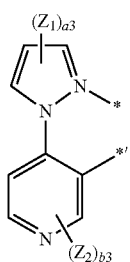
Formula 3-54
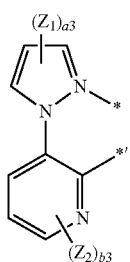
Formula 3-55
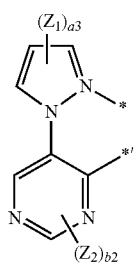
Formula 3-56
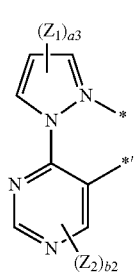
Formula 3-57
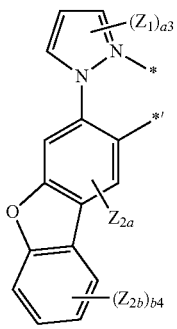
Formula 3-58
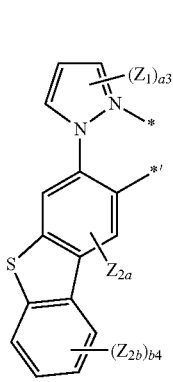
Formula 3-59
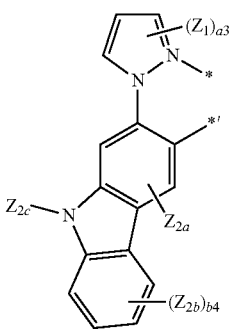
Formula 3-60
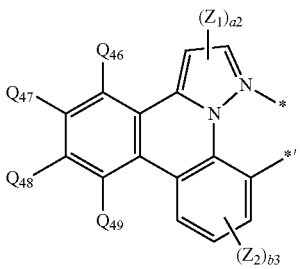
Formula 3-61
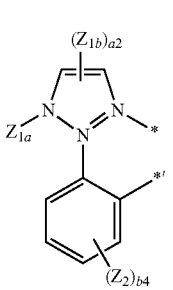

Formula 3-62
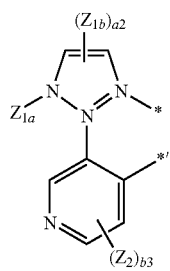
Formula 3-63
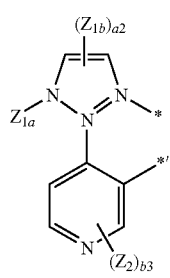
Formula 3-64
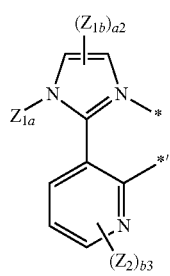
Formula 3-65
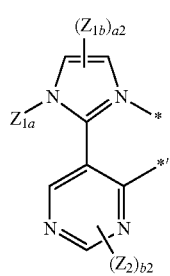
Formula 3-66
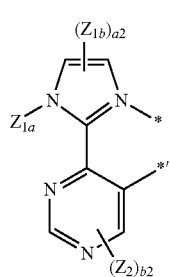
Formula 3-67
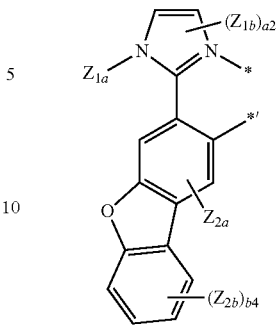
Formula 3-68
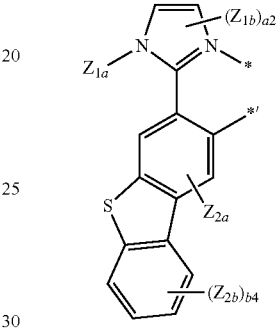
Formula 3-69
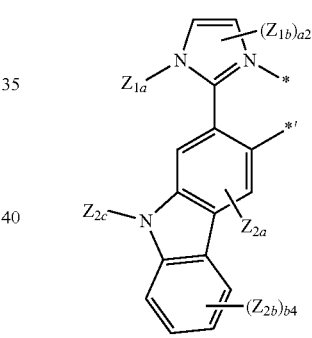
Formula 3-70
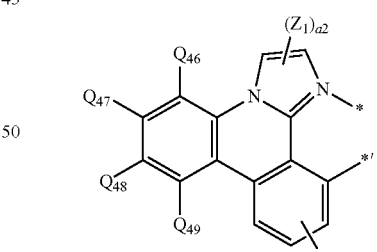
Formula 3-71
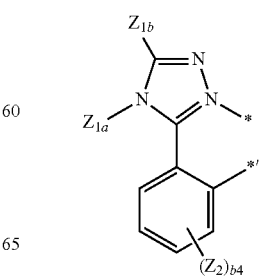

Formula 3-72
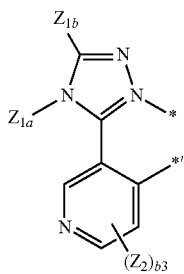
Formula 3-73
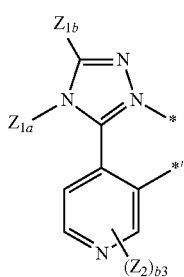
Formula 3-74
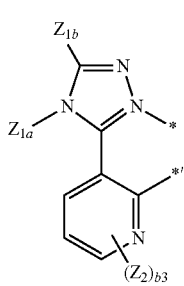
Formula 3-75
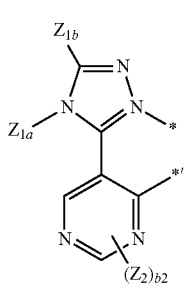
Formula 3-76
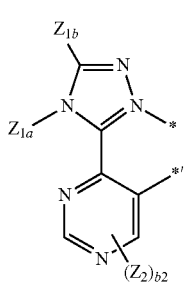
Formula 3-77
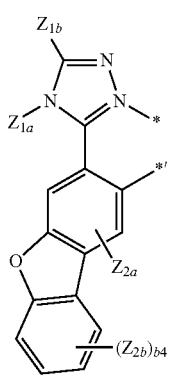
Formula 3-78
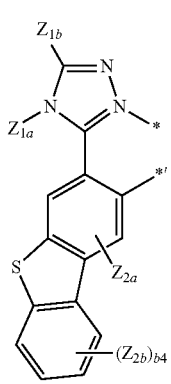
Formula 3-79
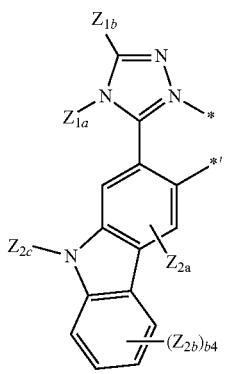
Formula 3-80
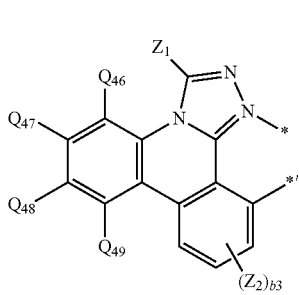

Formula 3-81
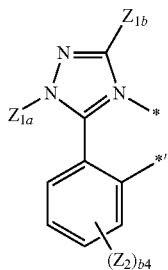
Formula 3-82
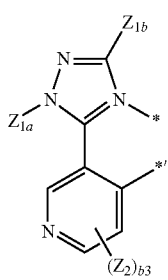
Formula 3-83
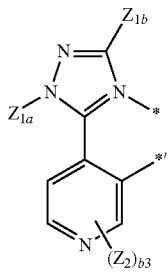
Formula 3-84
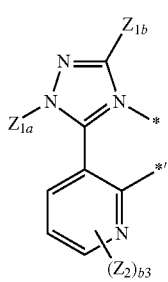
Formula 3-85
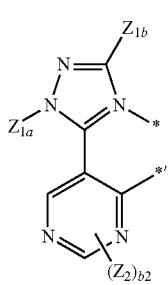
Formula 3-86
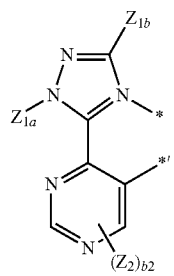
Formula 3-87
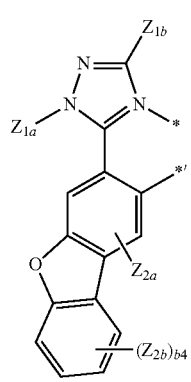
Formula 3-88
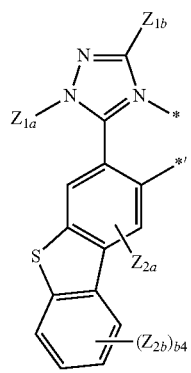
Formula 3-89
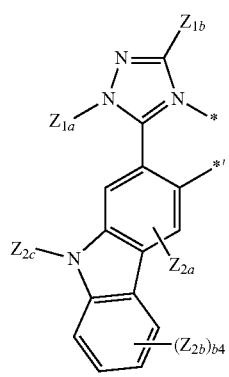

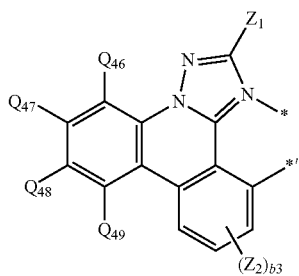
Formula 3-90
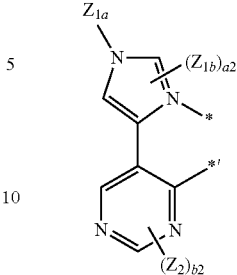
Formula 3-95
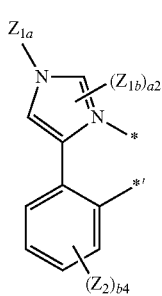
Formula 3-91
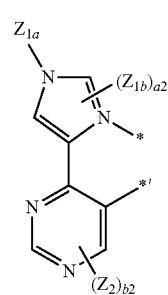
Formula 3-96
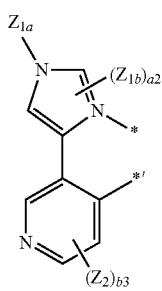
Formula 3-92
Formula 3-93
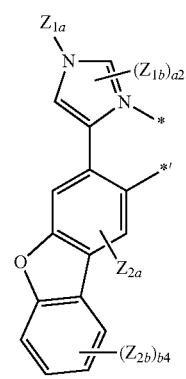
Formula 3-97
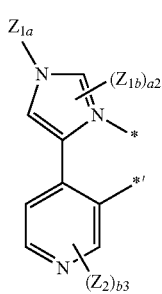
Formula 3-94
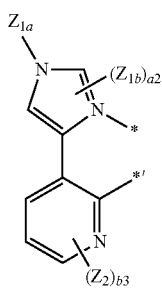
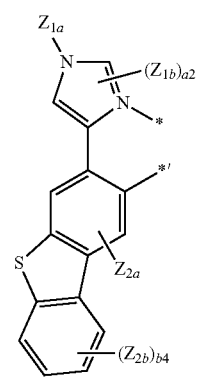
Formula 3-98

-continued
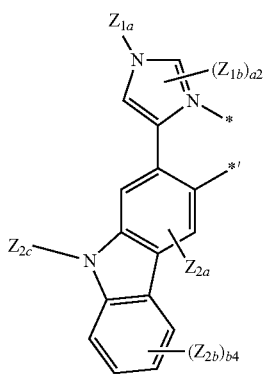
Formula 3-99
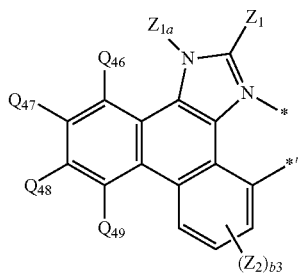
Formula 3-100
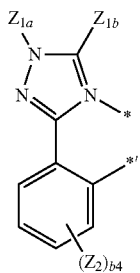
Formula 3-101
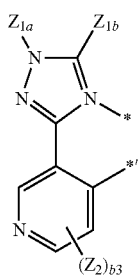
Formula 3-102
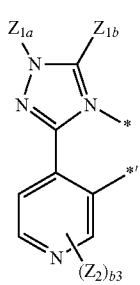
Formula 3-103
-continued
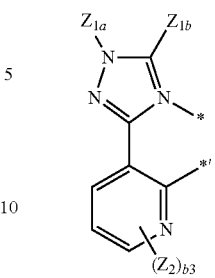
Formula 3-104
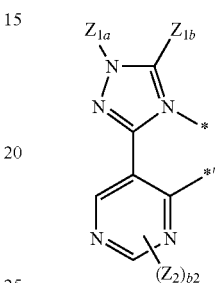
Formula 3-105
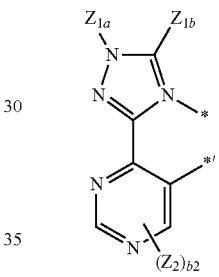
Formula 3-106
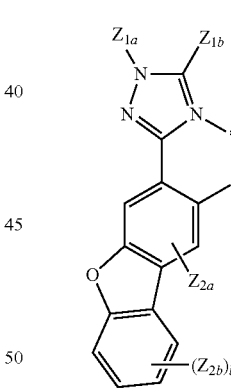
Formula 3-107
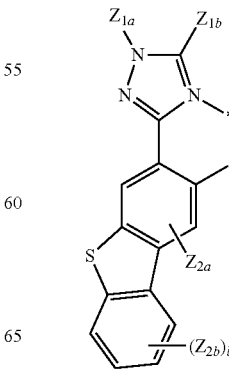
Formula 3-108

-continued
Formula 3-109
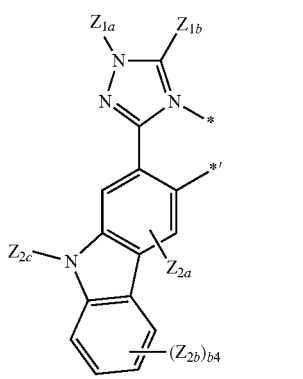
Formula 3-110
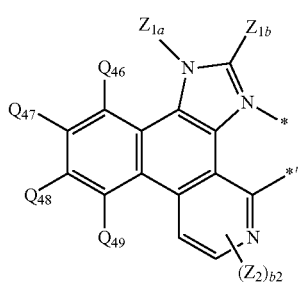
Formula 3-111
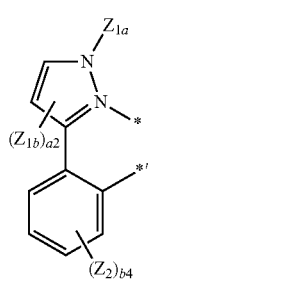
Formula 3-112
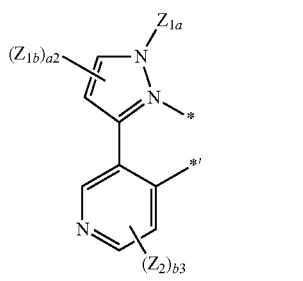
Formula 3-113
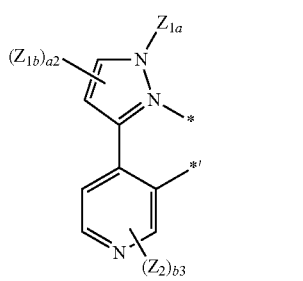
-continued
Formula 3-114
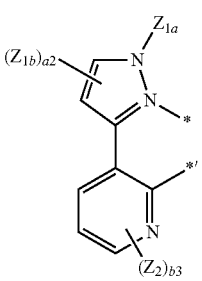
Formula 3-115
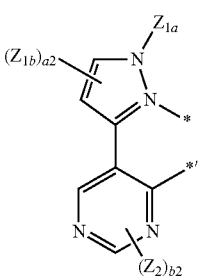
Formula 3-116
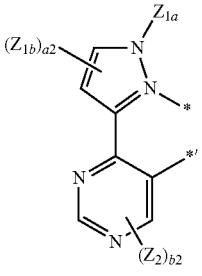
Formula 3-117
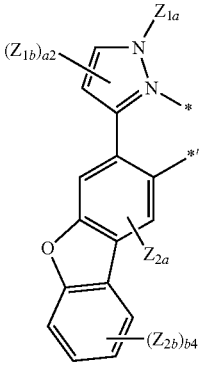
Formula 3-118
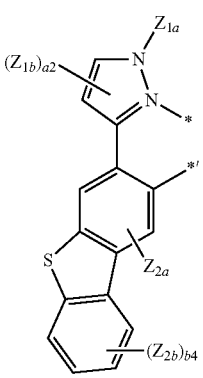

Formula 3-119 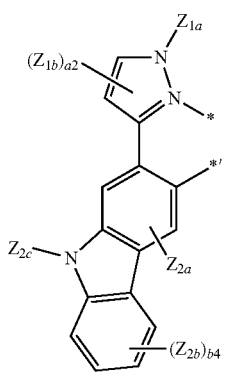
Formula 3-120 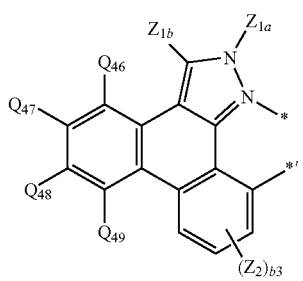
Formula 3-121 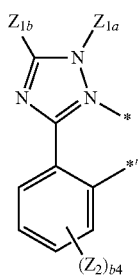
Formula 3-122 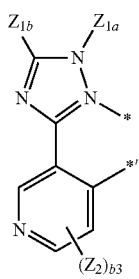
Formula 3-123 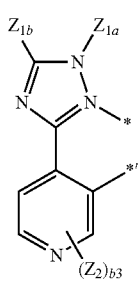
Formula 3-124 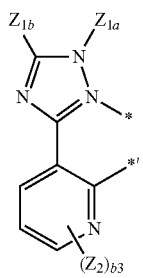
Formula 3-125 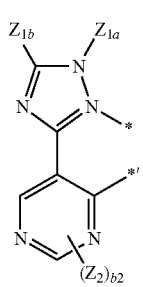
Formula 3-126 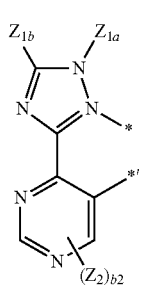
Formula 3-127 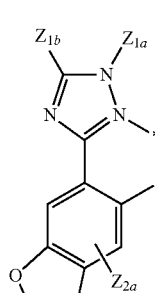
Formula 3-128 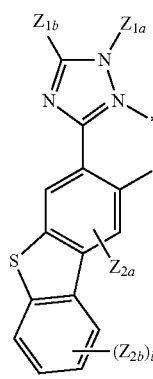

Formula 3-129
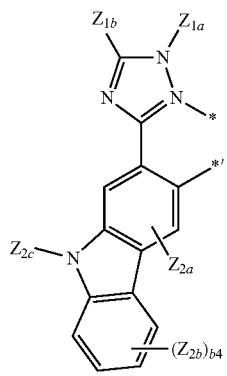
Formula 3-130
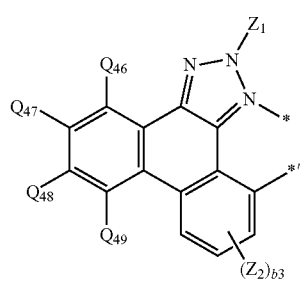
Formual 3-131
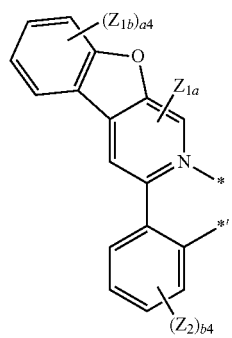
Formula 3-132
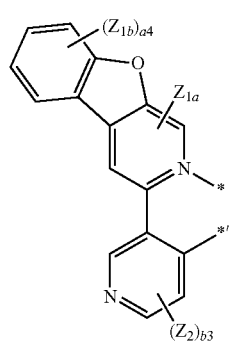
Formula 3-133
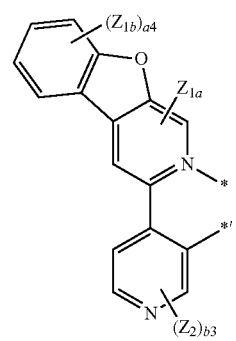
Formula 3-134
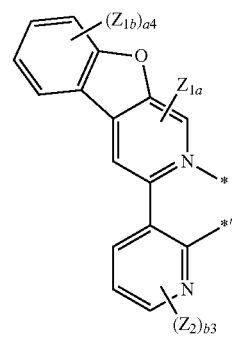
Formula 3-135
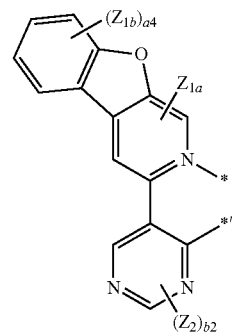
Formula 3-136
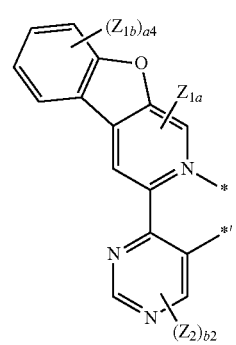

Examples of $Z_1$, $Z_2$, $Z_{1a}$, $Z_{1b}$, $Z_{2a}$, $Z_{2b}$, $Z_{2c}$, and $Q_{44}$ to $Q_{49}$ in Formulae 3-1 to 3-142 may be understood by referring to examples presented herein in connection with $R_1$.

For example, $Z_1$, $Z_2$, $Z_{1a}$, $Z_{1b}$, $Z_{2a}$, $Z_{2b}$, $Z_{2c}$, and $Q_{44}$ to $Q_{49}$ in Formulae 3-1 to 3-142 may be each independently selected from a hydrogen atom, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a pyridinyl group, a pyrimidinyl group, and a triazinyl group;

a phenyl group, a naphthyl group, a pyridinyl group, a pyrimidinyl group, and a triazinyl group;

a phenyl group, a naphthyl group, a pyridinyl group, a pyrimidinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, a triazinyl group, and —Si($Q_{33}$)($Q_{34}$)($Q_{35}$); and —Si($Q_3$)($Q_4$)($Q_5$), wherein $Q_3$ to $Q_5$ and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

In Formulae 3-1 to 3-142, a4 and b4 may be each independently 1, 2, 3, or 4;
a3 and b3 may be each independently 1, 2, or 3;
a2 and b2 may be each independently 1 or 2; and
* and *' are binding sites to M in Formula 1.

In some embodiments, $L_2$ in Formula 1 may be selected from a ligand represented by Formula 3-2, a ligand represented by Formula 3-132, and a ligand represented by Formula 4, and in Formulae 3-2, 3-132, and 4;

$X_{11}$ may be $C(R_{11})$,
$X_{12}$ may be $C(R_{12})$,
$X_{13}$ may be $C(R_{13})$, and
$X_{14}$ may be $C(R_{14})$;

$Z_1$, $Z_2$, $Z_{1a}$, $Z_{1b}$, and $R_{11}$ to $R_{14}$ may be each independently selected from a hydrogen atom, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a phenyl group, a naphthyl group, a pyridinyl group, a pyrimidinyl group, and a triazinyl group;

a phenyl group, a naphthyl group, a pyridinyl group, a pyrimidinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, a triazinyl group, and —Si($Q_{33}$)($Q_{34}$)($Q_{35}$); and —Si($Q_3$)($Q_4$)($Q_5$), wherein $Q_3$ to $Q_5$ and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

a4 and b4 may be each independently 1, 2, 3, or 4; a3 and b3 may be each independently 1, 2, or 3; a2 and b2 may be each independently 1 or 2; and * and *' are binding sites to M in Formula 1, but they are not limited thereto.

In some embodiments, $L_2$ in Formula 1 may be selected from a ligand represented by Formula 3-2A to a ligand represented by 3-2I and a ligand represented by Formula 4A, but is not limited thereto:

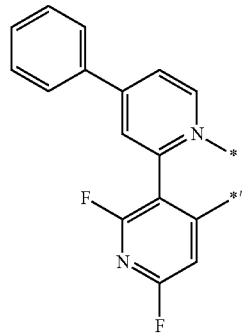

Formula 3-2A

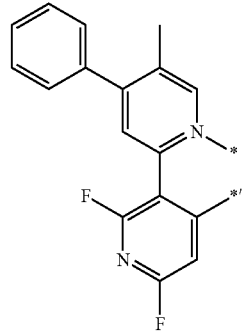

Formula 3-2B

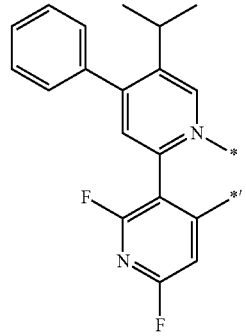

Formula 3-2C

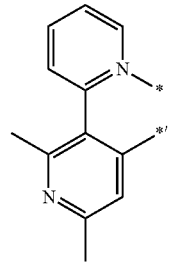

Formula 3-2D

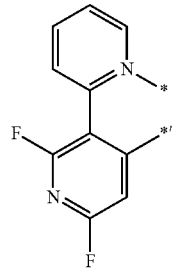

Formula 3-2E

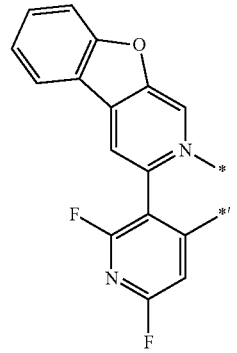

Formula 3-2F

-continued

Formula 3-2G

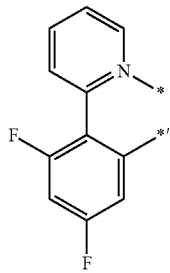

Formula 3-2H

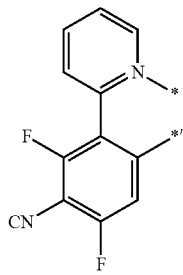

Formula 3-2I

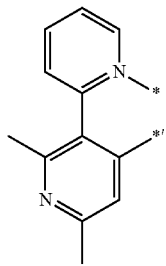

Formula 4A

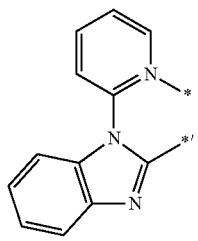

* and *' in Formulae 3-2A to 3-2I and 4A are binding sites to M in Formula 1.

In some embodiments, the organometallic compound may be represented by Formulae 1A or 1B below, but is not limited thereto:

Formula 1A

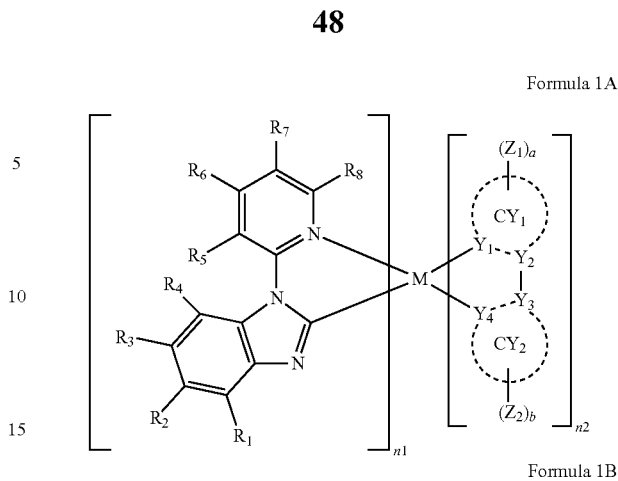

Formula 1B

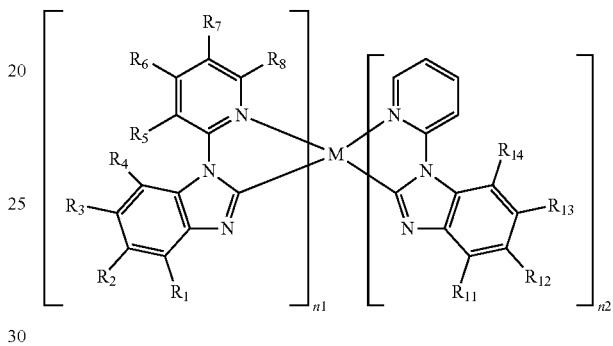

M, $R_1$ to $R_9$, $Z_1$, $Z_2$, a, b, $R_{11}$ to $R_{14}$, $Y_1$ to $Y_4$, $CY_1$, $CY_2$, n1, and n2 in Formulae 1A and 1B may be understood by referring to the description presented herein.

For example, in Formulae 1A and 1B, n1 may be 1, 2, or 3;

n2 may be 0, 1, or 2;

$Y_1$ to $Y_4$ are each independently carbon (C) or nitrogen (N);

$Y_1$ and $Y_2$ are linked to each other via a single bond or a double bond, and $Y_3$ and $Y_4$ are linked to each other via a single bond or a double bond;

$CY_1$ and $CY_2$ may be each independently a benzene, a naphthalene, a fluorene, a spiro-fluorene, an indene, a pyrrole, a thiophene, a furan, a imidazole, a pyrazole, a thiazole, an isothiazole, an oxazole, an isooxazole, a triazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzooxazole, an isobenzooxazole, a triazole, a tetrazole, an oxadiazole, a triazine, a dibenzofuran, a dibenzothiophene, a benzofuropyridine, or a benzothienopyridine;

$R_1$ to $R_8$, $Z_1$, $Z_2$, and $R_{11}$ to $R_{14}$ may be each independently selected from a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group;

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group, each substituted with at least one selected from —F, a cyano group, a nitro group, a phenyl group, a naphthyl group, a pyridinyl group, a pyrimidinyl group, a triazinyl group, and —Si$(Q_{33})(Q_{34})(Q_{35})$; and —Si$(Q_3)(Q_4)(Q_5)$, wherein $Q_3$ to $Q_5$ and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group, provided that each of $R_5$ to $R_8$ is not simultaneously a hydrogen;

a and b may be each independently 1, 2, or 3.

In some embodiments, in Formula 1A, $Y_1$ may be nitrogen (N), $Y_4$ may be carbon (C), $CY_1$ may be a pyridine, a triazole, an imidazole, a pyrazole, a benzofuropyridine, or a benzothienopyridine, and $CY_2$ may be a benzene or a pyridine, but they are not limited thereto.

n1 in Formula 1 indicates the number of $L_1$, and may be 1, 2, or 3, and when n1 is 2 or more, two or more $L_1$ may be identical or different.

n2 in Formula 1 indicates the number of $L_2$, and may be 0, 1, 2, 3, or 4, and when n2 is 2 or more, two or more $L_2$ may be identical or different.

In some embodiments, in Formula 1, n1 is 3, n2 is 0, and M is iridium; and i) $L_1$ includes only ligands represented by Formula 2A (in Formula 2A, $R_1$ to $R_4$ are a hydrogen, and $R_7$ is a phenyl group) and thus, three $L_1$ are identical, or ii) $L_1$ includes two ligands represented by Formula 2A (in Formula 2A, $R_1$ to $R_4$ are a hydrogen, and $R_7$ is a phenyl group) and one ligand represented by Formula 2B (in Formula 2B, $R_1$ to $R_4$ are a hydrogen, $R_6$ is a methyl group, and $R_7$ is a phenyl group).

In some other embodiments, in Formula 1, n1 is 1, n2 is 2, and M is iridium; and i) $L_2$ includes only two ligands represented by Formula 3-2A and thus, two $L_2$ may be identical, or ii) $L_2$ includes the ligand represented by Formula 3-2A and the ligand represented by Formula 3-2B and thus, two $L_2$ may be different.

The organometallic compound represented by Formula 1 may include any one selected from Compounds 1 to 33, but is not limited thereto:

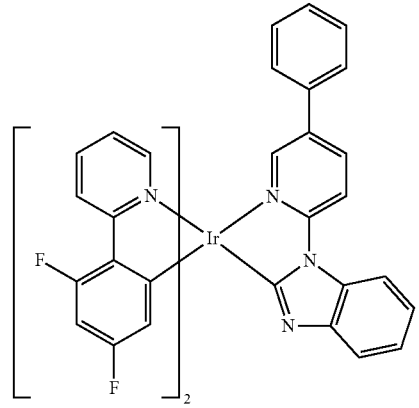

1

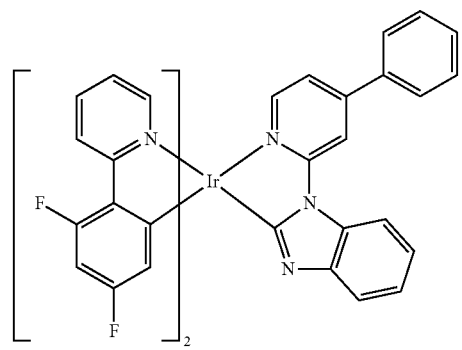

2

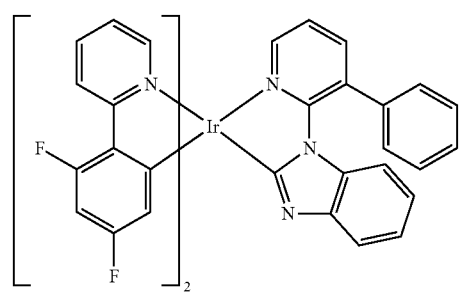

3

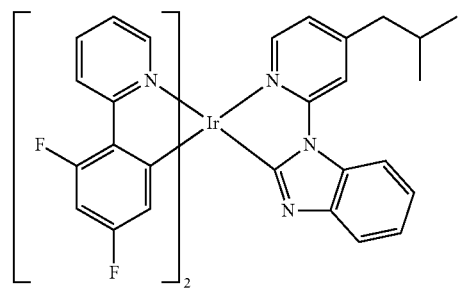

4

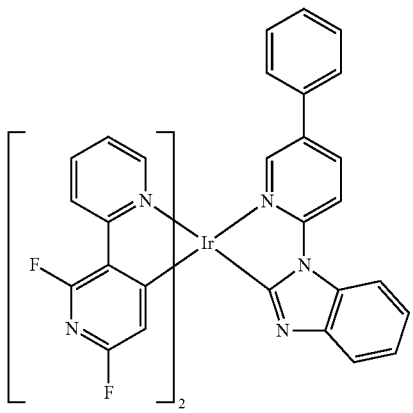
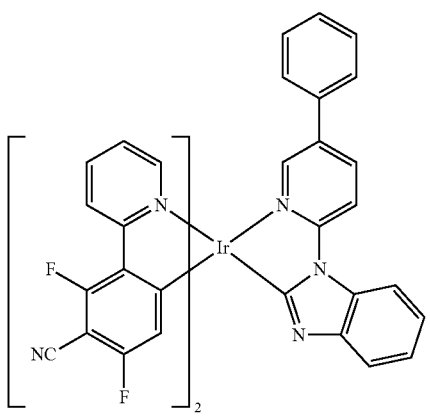
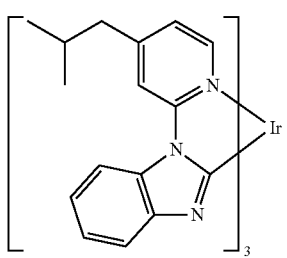
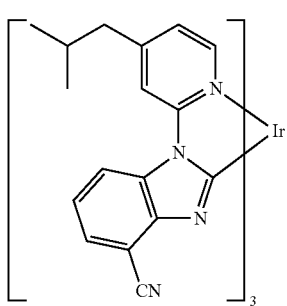
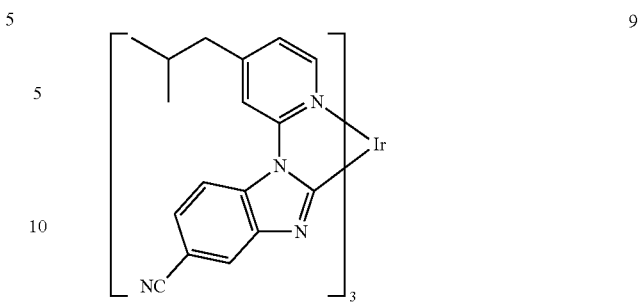
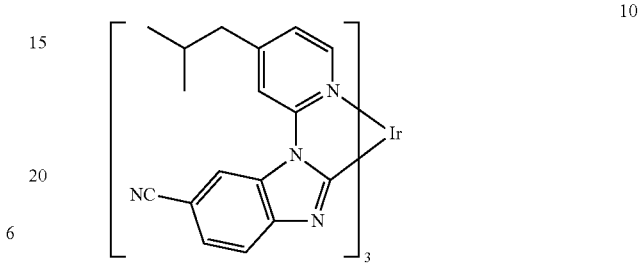
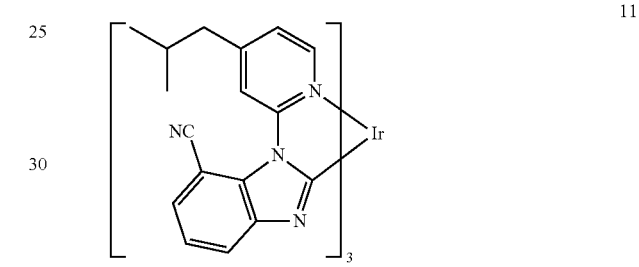
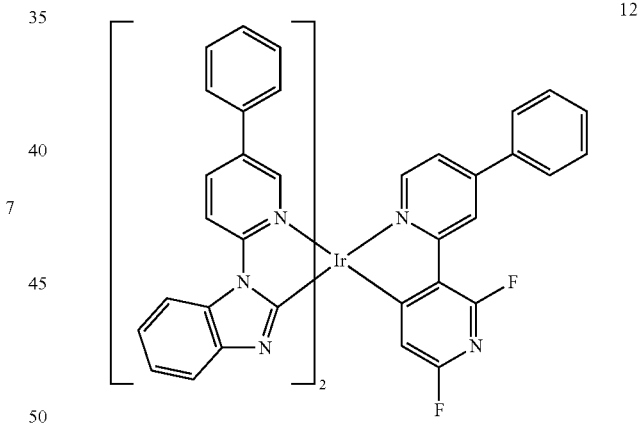
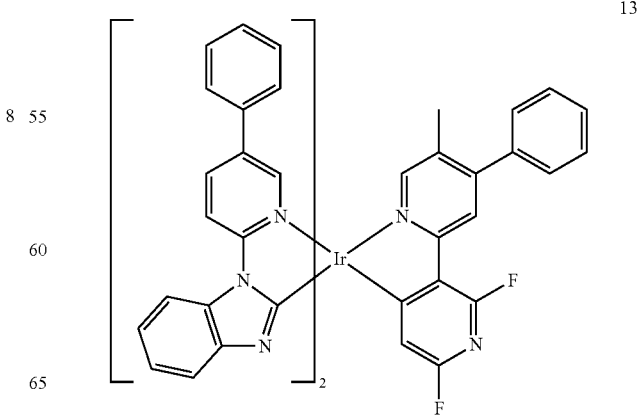

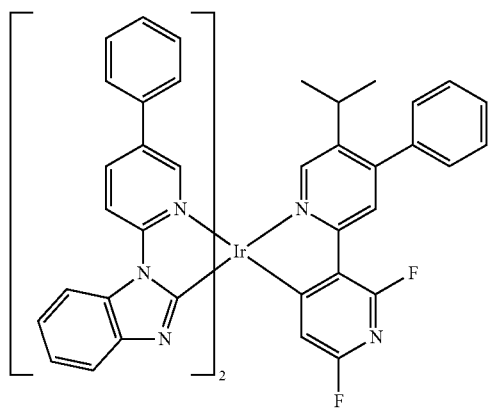
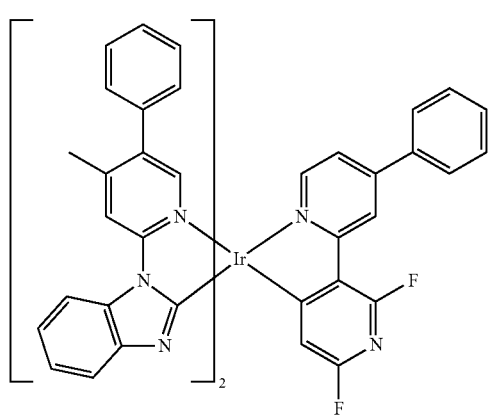
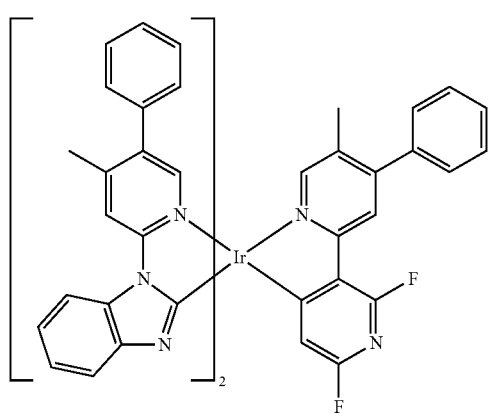
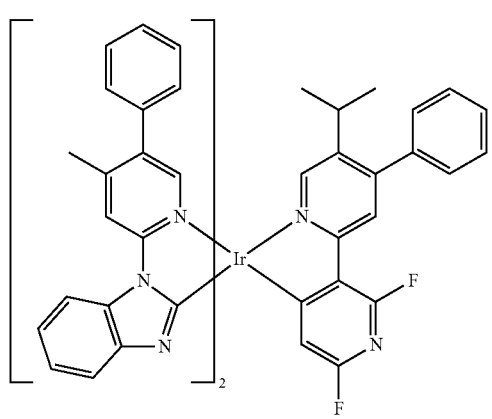
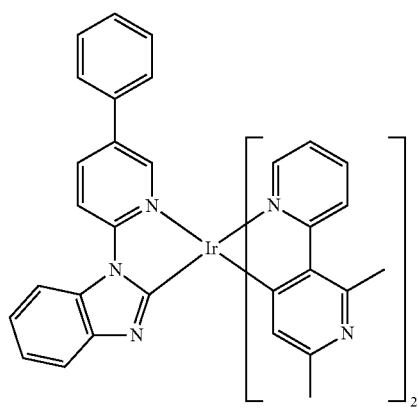
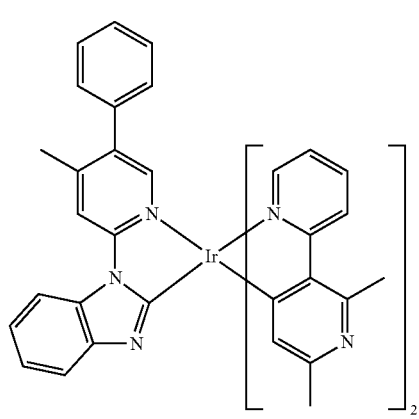
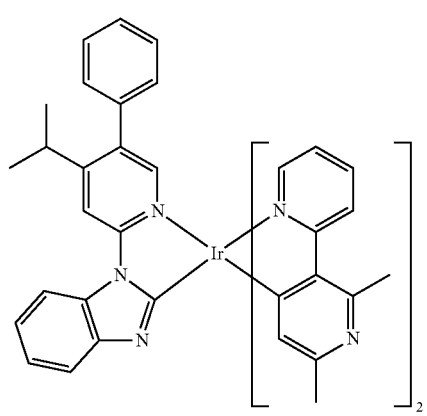
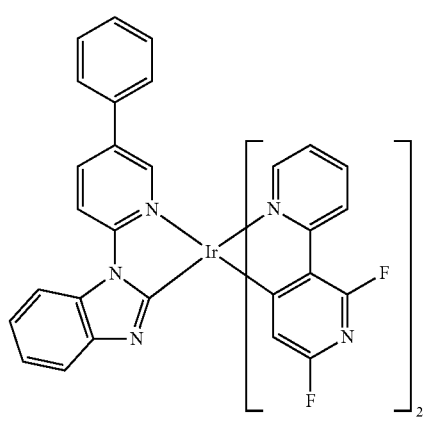

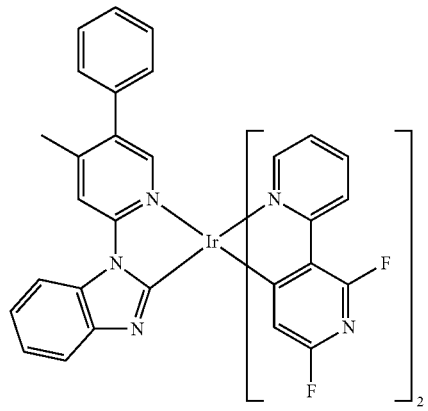
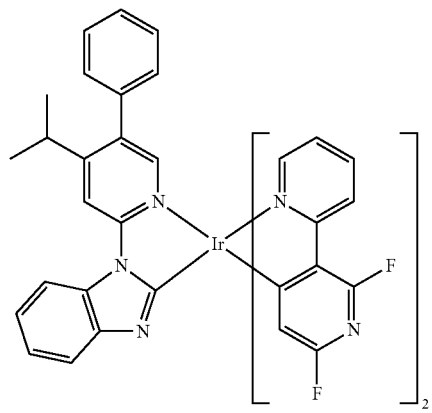
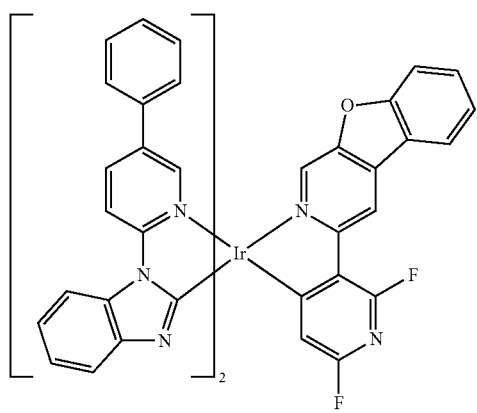
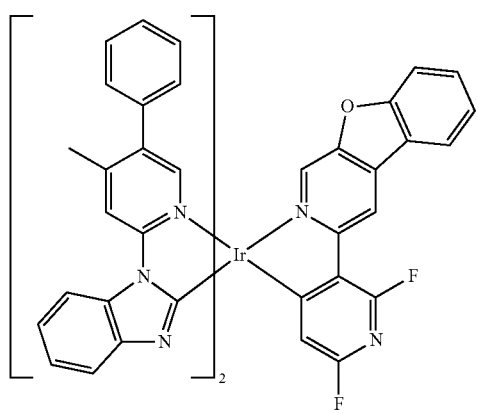
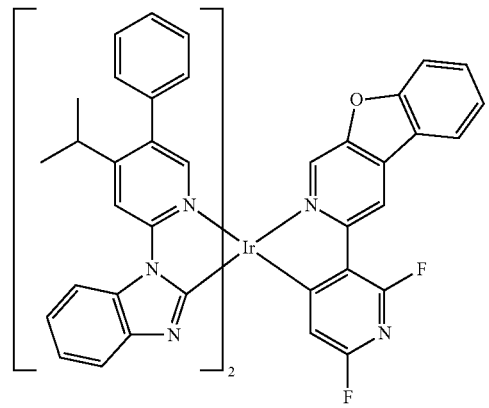
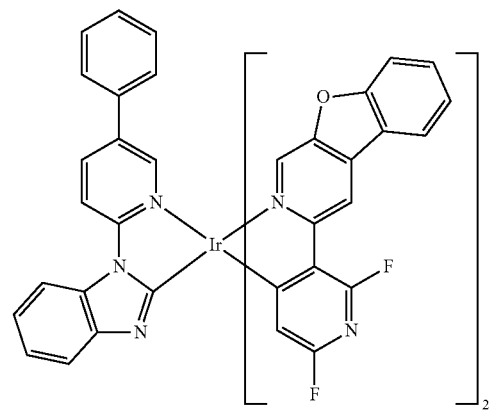
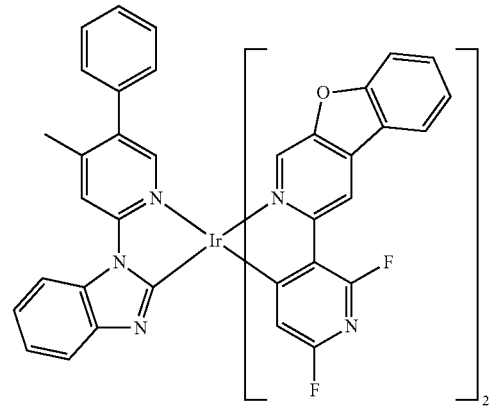
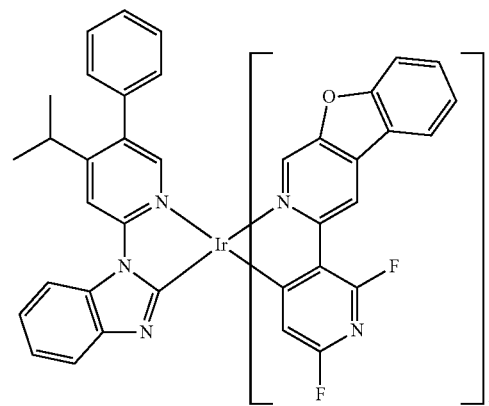

-continued

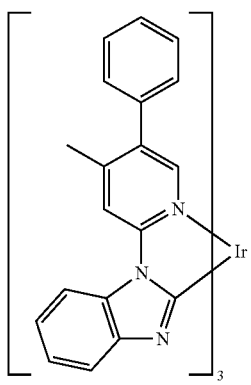

30

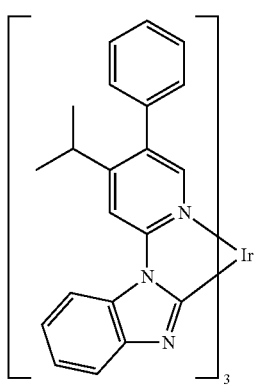

31

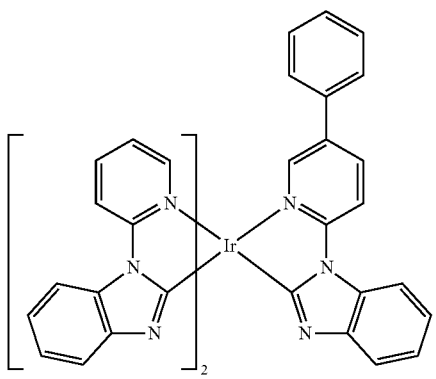

32

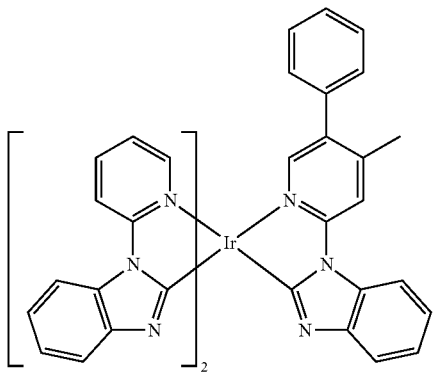

33

Since n1 of the organometallic compound represented by Formula 1, which indicates the number of $L_1$, is not zero, the organometallic compound represented by Formula 1 necessarily includes at least one ligand represented by Formula 2.

In Formula 2, a "pyridine-based ring" and a "benzimidazole-based ring" are linked to each other via an N—C bond (see Formula 2'). In Formula 2, each of $R_5$ to $R_8$, which are substituents of the "pyridine-based ring," cannot simultaneously be a hydrogen. That is, at least one of $R_5$ to $R_8$, which are substituents of the "pyridine-based ring" in Formula 2, is a substituent that is not a hydrogen. Accordingly, in the organometallic compound represented by Formula 1, stability due to electrons in a lowest unoccupied molecular orbital (LUMO) level may improve, and thus, the organometallic compound represented by Formula 1 may have excellent electrochemical stability. Thus, an organic light-emitting device including the organometallic compound represented by Formula 1 has high-purity blue emission, in addition to high efficiency, high brightness, and long lifespan.

Formula 2'

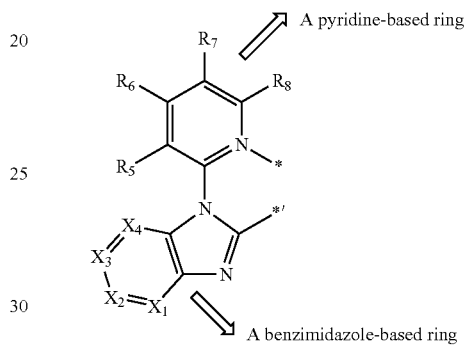

For example, the organometallic compound represented by Formula 1 enables emission of deep blue light which has a maximum emission wavelength of about 435 nanometers (nm) to about 500 nm, the x color coordinate of about 0.14 to about 0.20 (for example, in a range of about 0.14 to about 0.18) and the y color coordinate of about 0.10 to about 0.30 (for example, in a range of about 0.15 to about 0.25).

The highest occupied molecular orbital (HOMO), LUMO, singlet (S1) energy level, and triplet (T1) energy level of each of Compounds 1 to 33 were evaluated according to DFT method using Gaussian program (structural optimization was performed at B3LYP, 6-31G(d,p) levels), and the evaluation results are shown in Table 1 below.

TABLE 1

| Compound No. | HOMO (eV) | LUMO (eV) | $S_1$ energy level (eV) | $T_1$ energy level (eV) |
|---|---|---|---|---|
| 1 | −5.26 | −1.52 | 2.84 | 2.76 |
| 2 | −5.23 | −1.78 | 2.76 | 2.70 |
| 3 | −5.16 | −1.51 | 2.83 | 2.75 |
| 4 | −5.22 | −1.47 | 2.84 | 2.77 |
| 5 | −5.54 | −1.79 | 2.96 | 2.86 |
| 6 | −5.74 | −2.06 | 2.89 | 2.83 |
| 7 | −5.15 | −1.25 | 3.25 | 2.94 |
| 8 | −5.70 | −1.67 | 3.40 | 2.94 |
| 9 | −5.90 | −1.86 | 3.40 | 3.01 |
| 10 | −5.91 | −1.86 | 3.42 | 2.87 |
| 11 | −5.79 | −1.58 | 3.53 | 2.85 |
| 12 | −5.28 | −1.79 | 2.94 | 2.79 |
| 13 | −5.27 | −1.64 | 3.06 | 2.86 |
| 14 | −5.27 | −1.60 | 3.11 | 2.87 |
| 15 | −5.20 | −1.72 | 2.93 | 2.78 |
| 16 | −5.19 | −1.58 | 3.05 | 2.86 |
| 17 | −5.19 | −1.50 | 3.11 | 2.90 |
| 18 | −5.19 | −1.47 | 3.08 | 2.84 |
| 19 | −5.14 | −1.43 | 3.08 | 2.84 |

TABLE 1-continued

| Compound No. | HOMO (eV) | LUMO (eV) | $S_1$ energy level (eV) | $T_1$ energy level (eV) |
|---|---|---|---|---|
| 20 | −5.13 | −1.42 | 3.08 | 2.84 |
| 21 | −5.52 | −1.78 | 3.14 | 2.89 |
| 22 | −5.47 | −1.74 | 3.14 | 2.96 |
| 23 | −5.46 | −1.73 | 3.14 | 2.96 |
| 24 | −5.28 | −1.92 | 2.85 | 2.72 |
| 25 | −5.20 | −1.86 | 2.83 | 2.70 |
| 26 | −5.18 | −1.84 | 2.83 | 2.70 |
| 27 | −5.44 | −2.03 | 2.92 | 2.77 |
| 28 | −5.40 | −2.00 | 2.91 | 2.76 |
| 29 | −5.39 | −1.99 | 2.91 | 2.76 |
| 30 | −5.13 | −1.29 | 3.22 | 2.97 |
| 31 | −5.11 | −1.27 | 3.22 | 3.01 |
| 32 | −5.25 | −1.48 | 3.13 | 2.89 |
| 33 | −5.21 | −1.40 | 3.17 | 2.97 |

Referring to Table 1, it is confirmed that Compounds 1 to 33 have HOMO, LUMO, $S_1$ energy levels and $T_1$ energy level that are suitable for use as a material for an organic light-emitting device. Accordingly, the organometallic compound represented by Formula 1 has electric characteristics that are suitable for use as a material for an organic light-emitting device.

Synthesis methods of the organometallic compound represented by Formula 1 may be apparent to one of ordinary skill in the art by referring to Synthesis Examples provided below.

The organometallic compound represented by Formula 1 is suitable for use in an organic layer of an organic light-emitting device, for example, for use as a dopant in an emission layer of the organic layer. Thus, another aspect provides an organic light-emitting device that includes:

a first electrode;

a second electrode; and an organic layer that is disposed between the first electrode and the second electrode, wherein the organic layer including an emission layer and at least one of the organometallic compound represented by Formula 1.

The organic light-emitting device may have, due to the inclusion of an organic layer including the organometallic compound represented by Formula 1, low driving voltage, high efficiency, high brightness, and long lifespan. An organic light-emitting device including the organometallic compound represented by Formula 1 enables emission of deep blue light which has a maximum emission wavelength of about 435 nm to about 500 nm, the x color coordinate of about 0.14 to about 0.20 (for example, in a range of about 0.14 to about 0.18) and the y color coordinate of about 0.10 to about 0.25 (for example, in a range of about 0.15 to about 0.25).

The organometallic compound of Formula 1 may be used between a pair of electrodes of an organic light-emitting device. For example, the organometallic compound represented by Formula 1 may be included in the emission layer. In this regard, the organometallic compound may act as a dopant, and the emission layer may further include a host (that is, an amount of the organometallic compound represented by Formula 1 may be smaller than that of the host).

The expression "(an organic layer) includes at least one organometallic compounds" used herein may include a case in which "(an organic layer) includes identical organometallic compounds of Formula 1 and a case in which (an organic layer) includes two or more different organometallic compounds of Formula 1.

For example, the organic layer may include, as the organometallic compound, only Compound 1. In this regard, Compound 1 may be situated in an emission layer of the organic light-emitting device. In some embodiments, the organic layer may include, as the organometallic compound, Compound 1 and Compound 2. In this regard, Compound 1 and Compound 2 may be situated in an identical layer (for example, Compound 1 and Compound 2 all may be situated in an emission layer).

The first electrode may be an anode, which is a hole injection electrode, and the second electrode may be a cathode, which is an electron injection electrode, or the first electrode may be a cathode, which is an electron injection electrode, or the second electrode may be an anode, which is a hole injection electrode.

For example, the first electrode may be an anode, and the second electrode may be a cathode, and the organic layer may include i) a hole transport region that is disposed between the first electrode and the emission layer, wherein the hole transport region includes at least one of a hole injection layer, a hole transport layer, and an electron blocking layer, and ii) an electron transport region that is disposed between the emission layer and the second electrode, wherein the electron transport region includes at least one selected from a hole blocking layer, an electron transport layer, and an electron injection layer.

The term "organic layer" used herein refers to a single layer and/or a plurality of layers disposed between the first electrode and the second electrode of an organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or transparent plastic substrate, each with excellent mechanical strength, thermal stability, transparency, surface smoothness, ease of handling, and water repellency.

The first electrode 11 may be formed by depositing or sputtering a material for forming the first electrode on the substrate. The first electrode 11 may be an anode. The material for the first electrode 11 may be selected from materials with a high work function to make holes be easily injected. The first electrode 11 may be a reflective electrode, a semi-transmissive electrode, or a transmissive electrode. The material for the first electrode 11 may be indium tin oxide (ITO), indium zinc oxide (IZO), tin oxide ($SnO_2$), zinc oxide (ZnO), or the like. In some embodiments, magnesium (Mg), aluminum (Al), aluminum-lithium (Al—Li), calcium (Ca), magnesium-indium (Mg—In), or magnesium-silver (Mg—Ag) may be used.

The first electrode 11 may have a single-layer structure or a multi-layer structure including two or more layers. For example, the first electrode 11 may have a three-layered structure of ITO/Ag/ITO, but the structure of the first electrode 11 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one of a hole injection layer, a hole transport layer, an electron blocking layer, and a buffer layer.

The hole transport region may include only either a hole injection layer or a hole transport layer. The hole injection layer may have a single-layer structure or a multi-layer structure. For example, the hole transport region may have a structure of hole injection layer/hole transport layer, a structure of hole injection layer/hole transport layer/electron blocking layer, and a structure of first hole injection layer/second hole injection layer/electron blocking layer, each stacked in this stated order on the first electrode 11, but the structure of the hole transport region is not limited thereto.

When the hole transport region includes a hole injection layer (HIL), the hole injection layer may be formed on the first electrode 11 by using various methods, such as vacuum deposition, spin coating, casting, or Langmuir-Blodgett (LB).

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

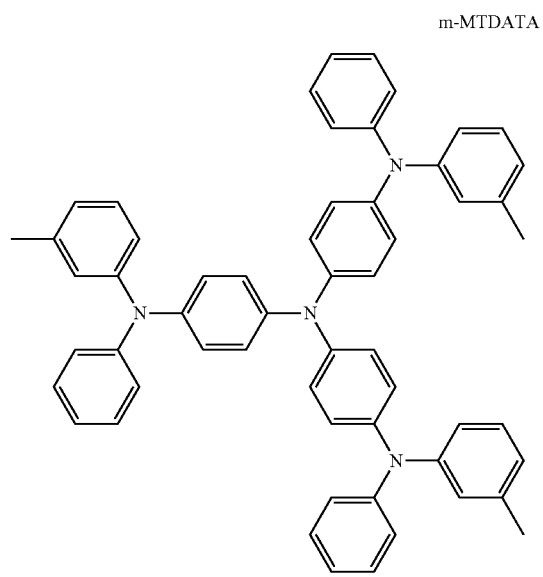

m-MTDATA

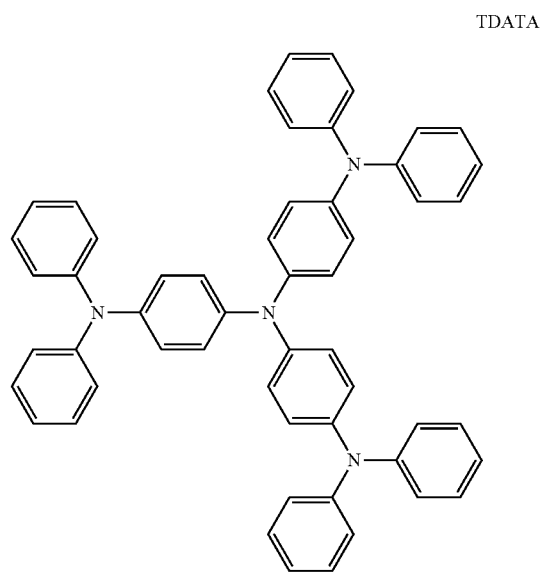

TDATA

2-TNATA
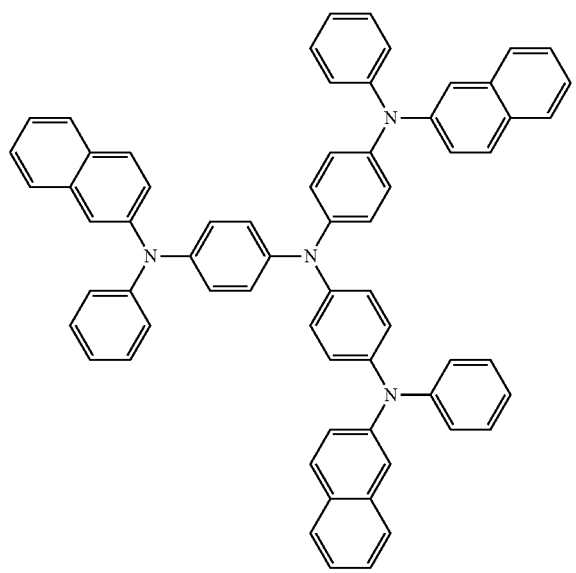
NPB
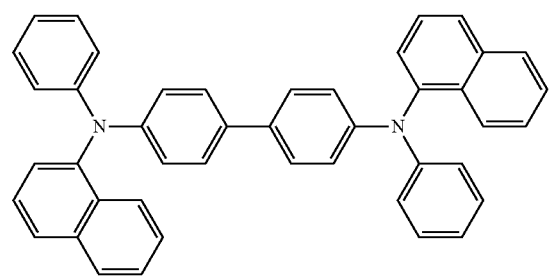
β-NPB
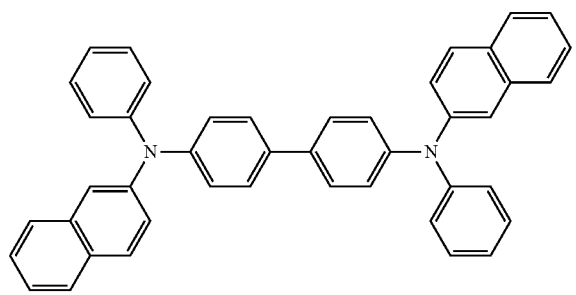
TPD
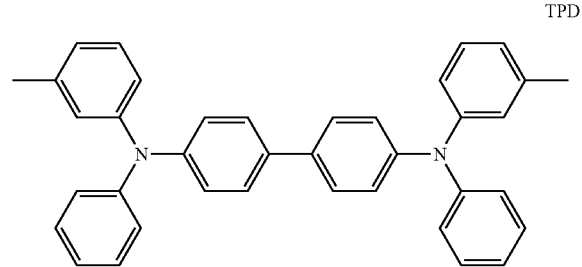
Spiro-TPD
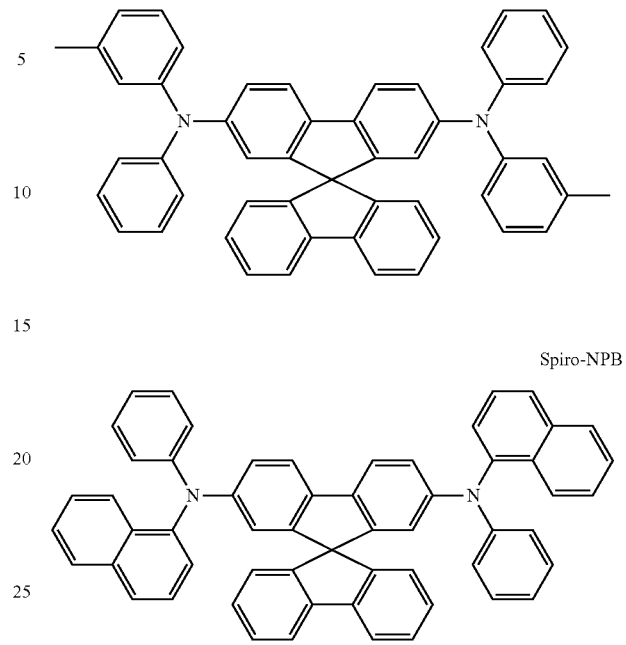
Spiro-NPB
methylated NPB
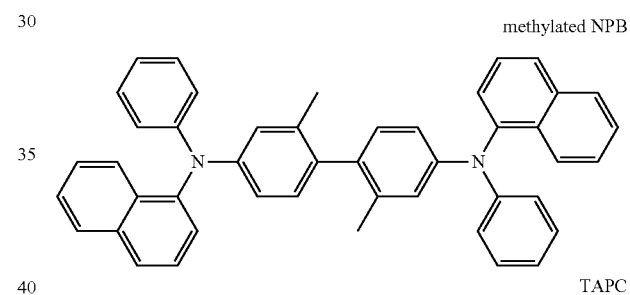
TAPC
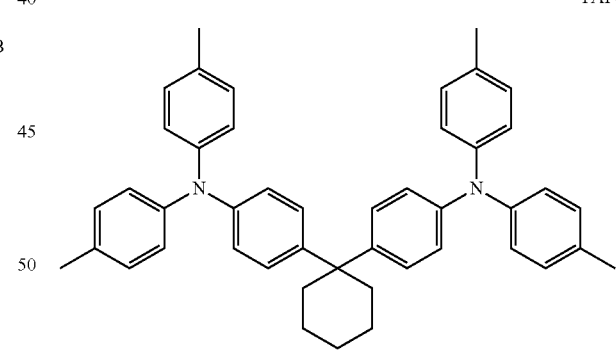
HMTPD
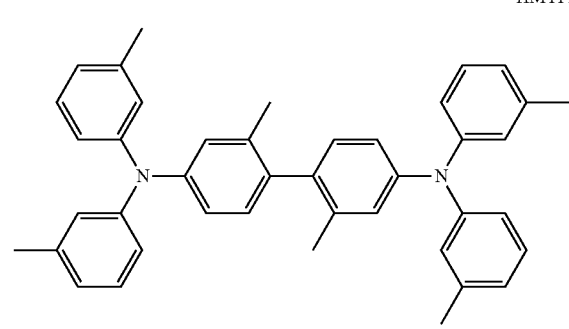

Formula 201

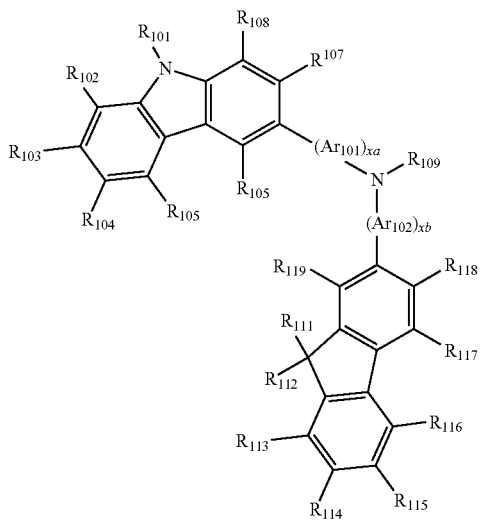

Formula 202

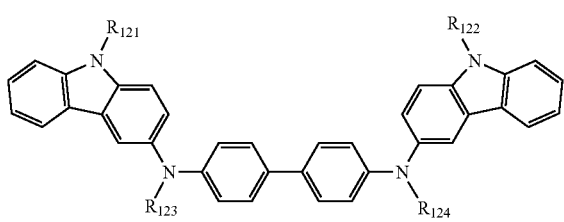

$Ar_{101}$ to $Ar_{102}$ in Formula 201 may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

In Formula 201, xa and xb may be each independently an integer of 0 to 5, for example 0, 1, or 2. For example, xa may be 1 and xb may be 0, but they are not limited thereto.

$R_{101}$ to $R_{108}$, $R_{111}$ to $R_{119}$ and $R_{121}$ to $R_{124}$ in Formulae 201 and 202 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$alkyl group (for example, a methyl group, an ethyl group, a propyl group, a butyl group, a pentyl group, a hexyl group, and so on), and a $C_1$-$C_{10}$ alkoxy group (for example, a methoxy group, an ethoxy group, a propoxy group, a butoxy group, or a pentoxy group);

a $C_1$-$C_1$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, or a $C_1$-$C_{10}$ alkoxy group, but they are not limited thereto.

$R_{109}$ in Formula 201 may be selected from a phenyl group, a naphthyl group, an anthracenyl group and a pyridinyl group; and a phenyl group, a naphthyl group, an anthracenyl group and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, and a pyridinyl group.

According to an embodiment, the compound represented by Formula 201 may be represented by Formula 201A, but is not limited thereto:

Formula 201A

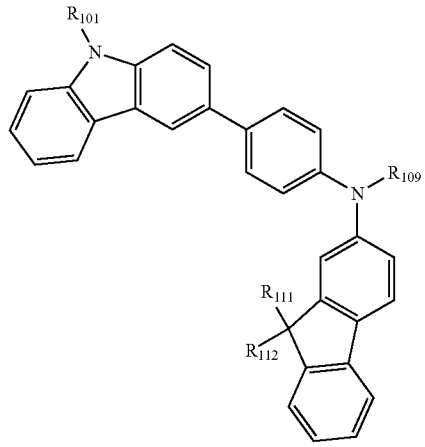

$R_{101}$, $R_{111}$, $R_{112}$, and $R_{109}$ in Formula 201A may be understood by referring to the description provided herein.
For example, the compound represented by Formula 201, and the compound represented by Formula 202 may include compounds HT1 to HT20 illustrated below, but are not limited thereto.
HT1
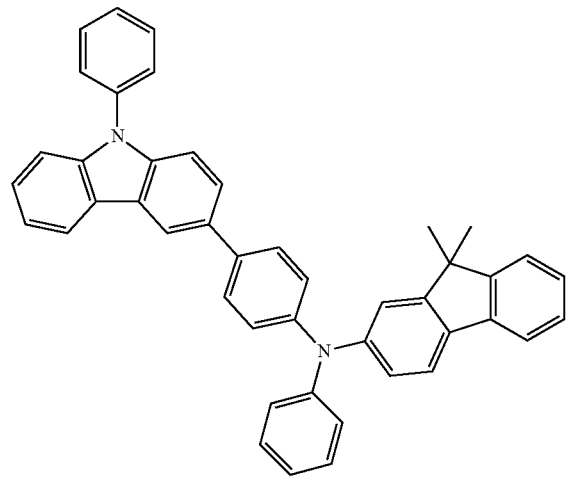
HT2
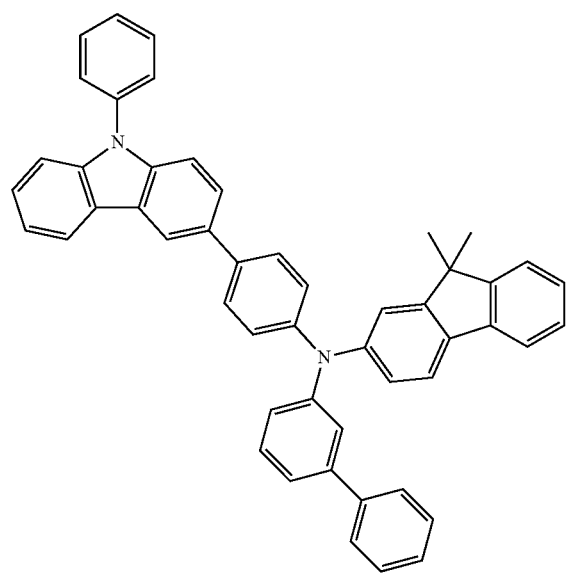
HT3
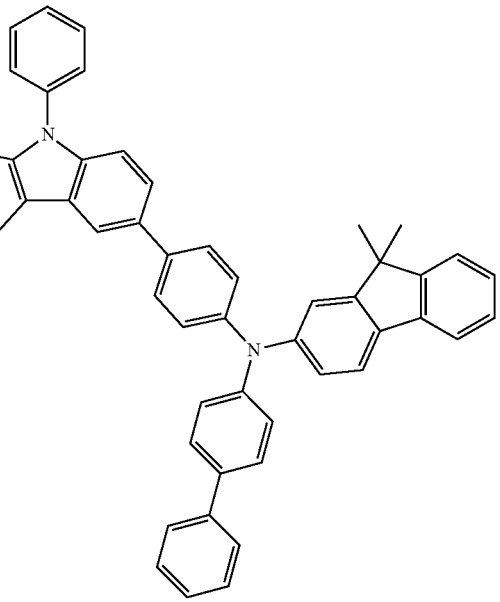
HT4
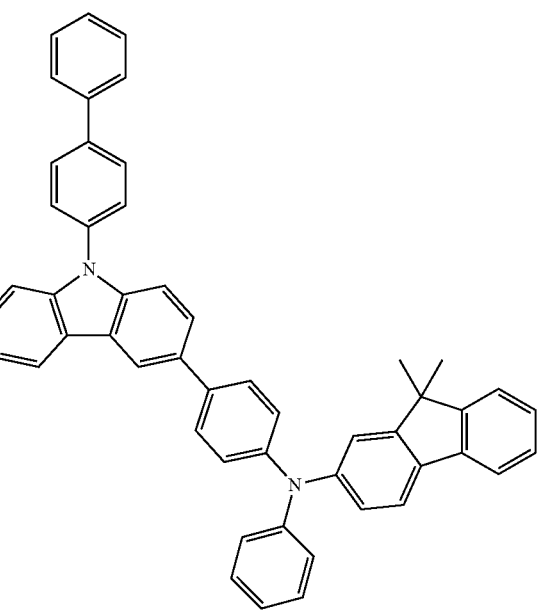

HT5
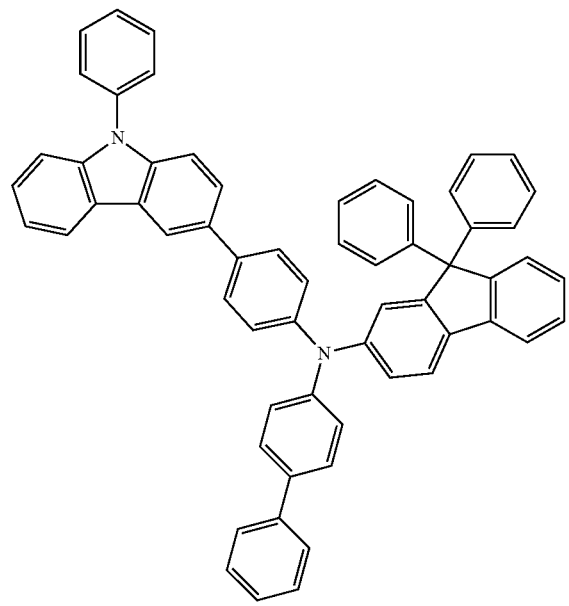
HT6
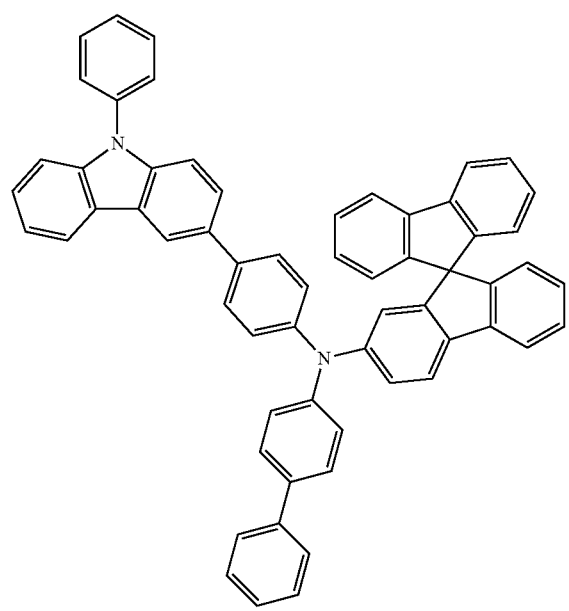
HT7
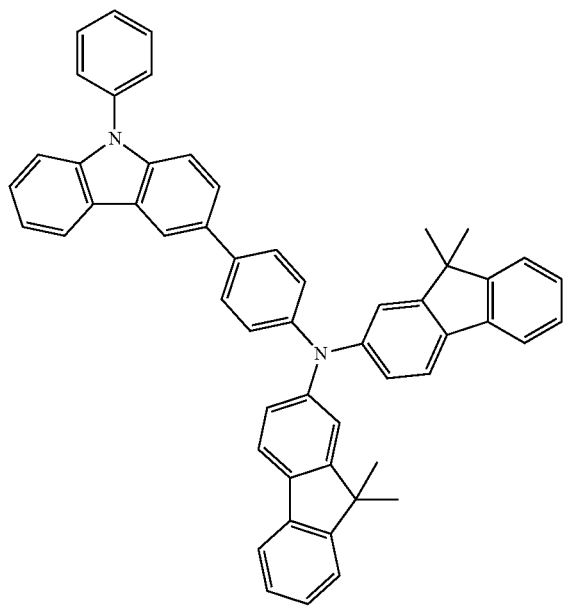
HT8
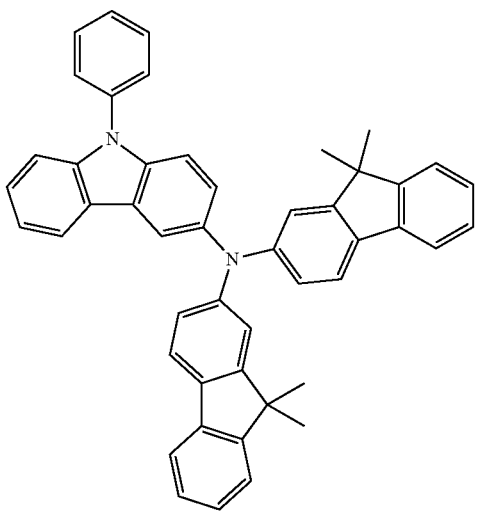
HT9

HT10
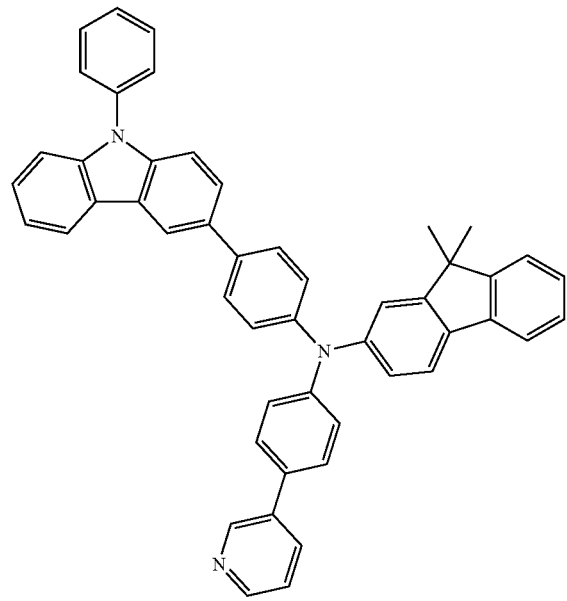
HT11
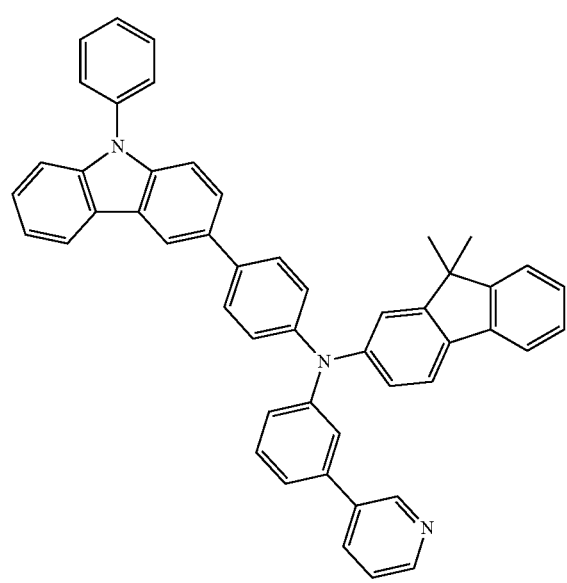
HT12
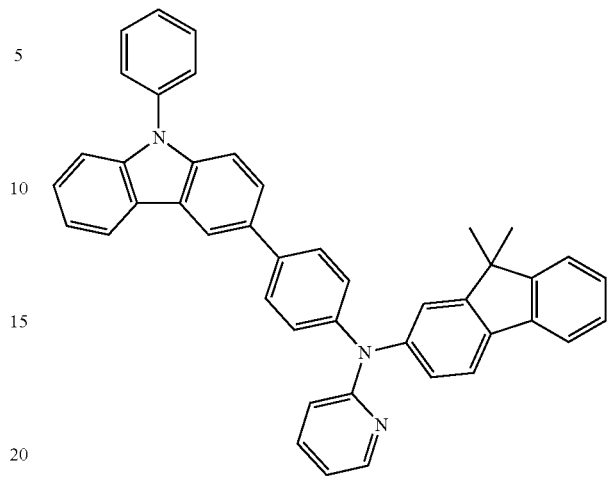
HT13
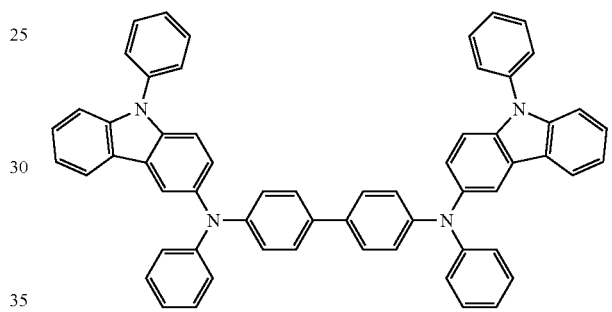
HT14
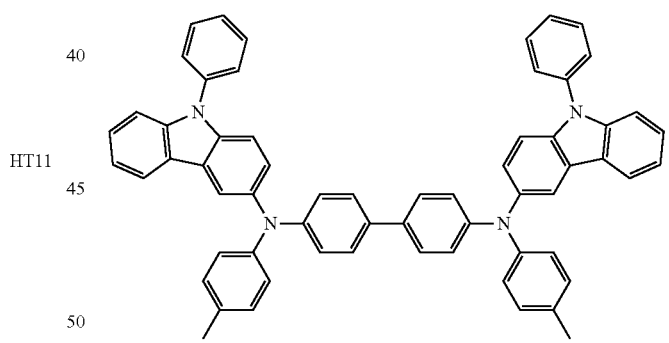
HT15
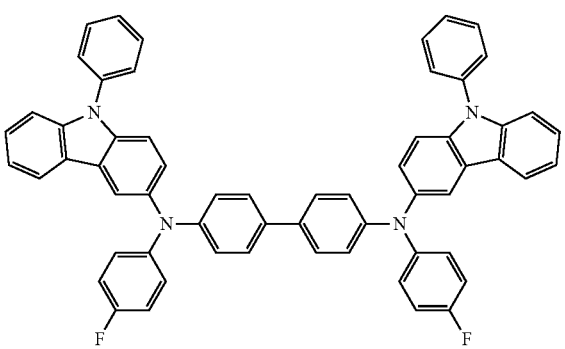

HT16

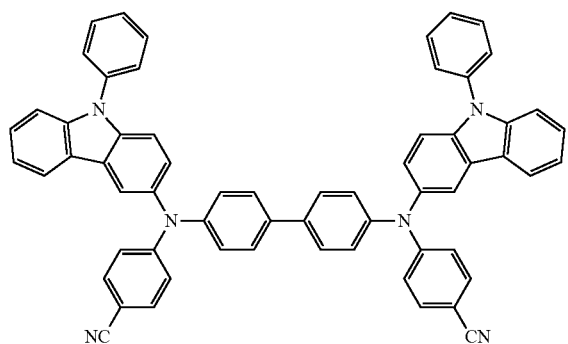

HT20

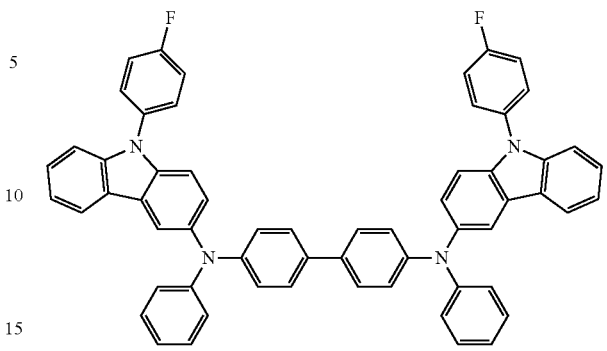

HT17

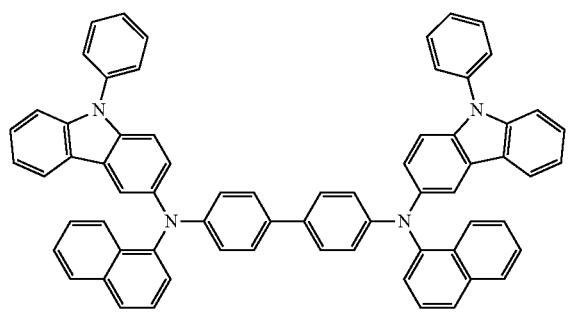

A thickness of the hole transport region may be in a range of about 100 Å to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

For example, the hole transport region may include a first hole injection layer and a second hole injection layer, and the second hole injection layer may include the electron-generation material alone or together with other materials.

The charge-generation material may be, for example, a p-dopant. The p-dopant may be one of a quinone derivative, a metal oxide, and a cyano group-containing compound, but is not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 or Compound HT-D2 below, but are not limited thereto.

HT18

HT19

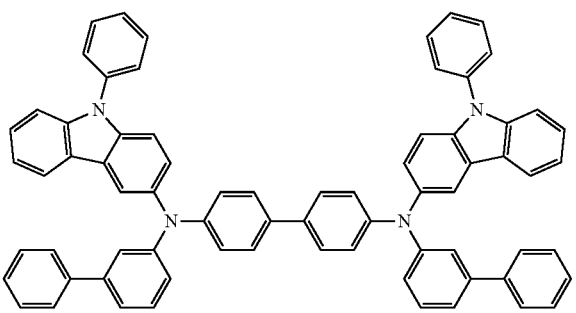

Compound HT-D1

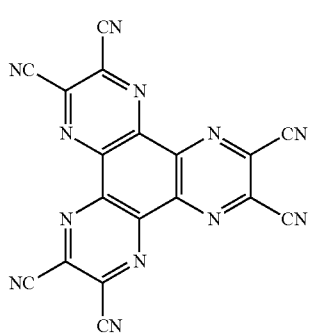

F4-TCNQ

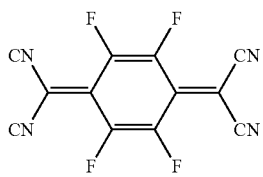

Compound HT-D2

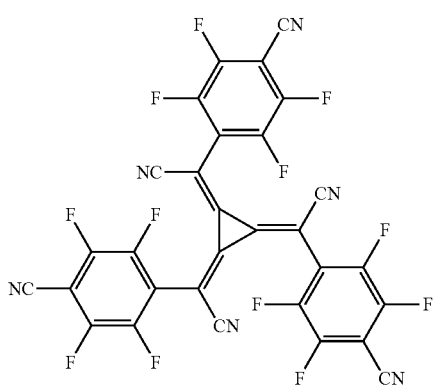

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

The emission layer may include a host and a dopant, and the dopant may include the organometallic compound represented by Formula 1.

The host may be any known host. The host may include, for example, identical compounds or two different compounds.

For example, the host may be CBP, CDBP, TCP, or mCP, but is not limited thereto.

CBP

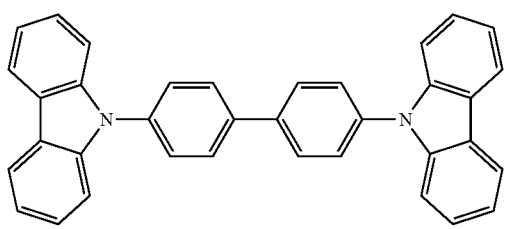

CDBP

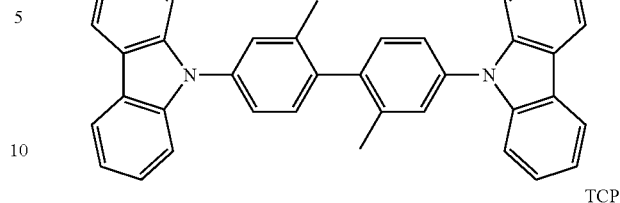

TCP mCP

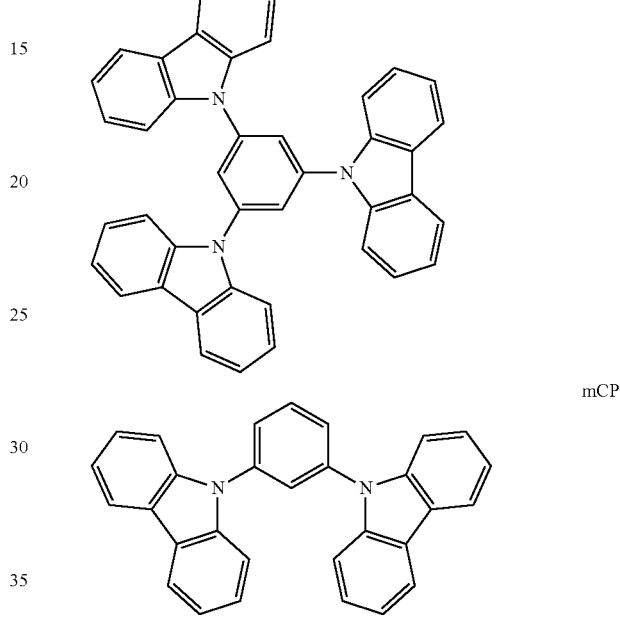

When the organic light-emitting device is a full color organic light-emitting device, the emission layer may be patterned into a red emission layer, a green emission layer, and a blue emission layer. According to another embodiment, due to a stacked structure including a red emission layer, a green emission layer, and/or a blue emission layer, the emission layer may emit white light.

When the emission layer includes a host and a dopant, an amount of the dopant may be in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layer structure including two or more different materials.

Conditions for forming the hole blocking layer, the electron transport layer, and the electron injection layer which constitute the electron transport region may be understood by referring to the conditions for forming the hole injection layer.

When the electron transport layer includes a hole blocking layer, the hole blocking layer may include, for example, at least one of BCP and Bphen, but may also include other materials.

BCP

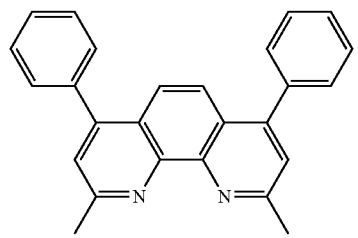

Bphen

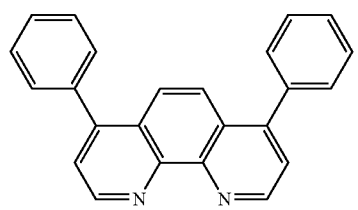

A thickness of the hole blocking layer may be in a range of about 20 Å to about 1,000 Å, for example, about 30 Å to about 300 Å. When the thickness of the hole blocking layer is within these ranges, the hole blocking layer may have improved hole blocking ability without a substantial increase in driving voltage.

The electron transport layer may further include at least one selected from BCP, Bphen, Alq$_3$, Balq, TAZ, and NTAZ.

Alq$_3$

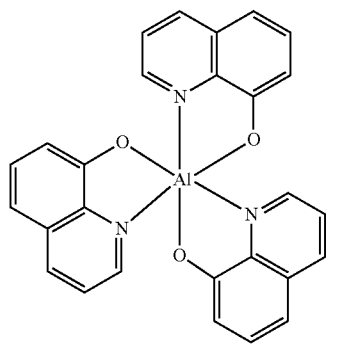

BAlq

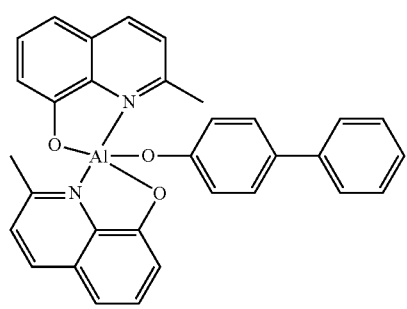

TAZ

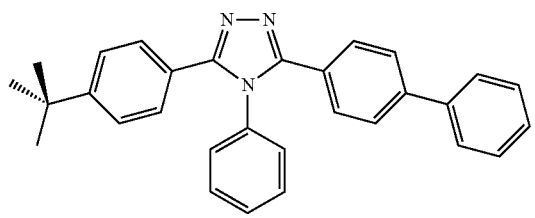

NTAZ

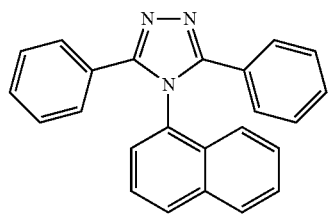

In some embodiments, the electron transport layer may include at least one selected from ET1 and ET19, but are not limited thereto.

ET1

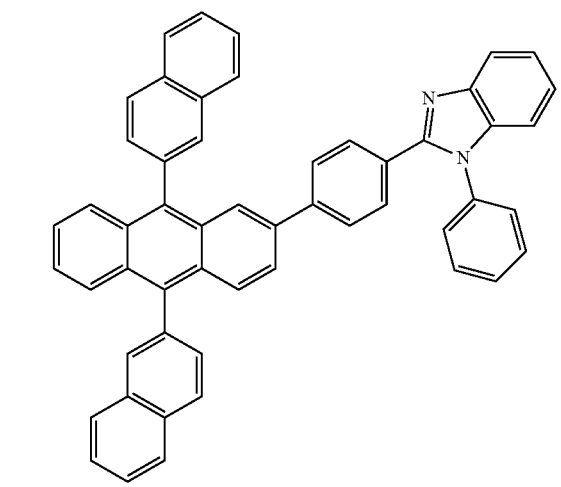

ET2

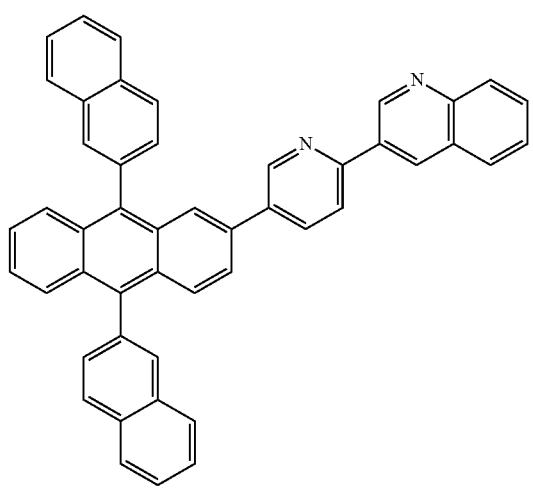

ET3
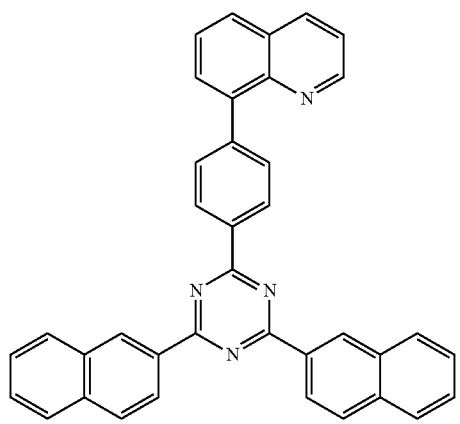
ET6
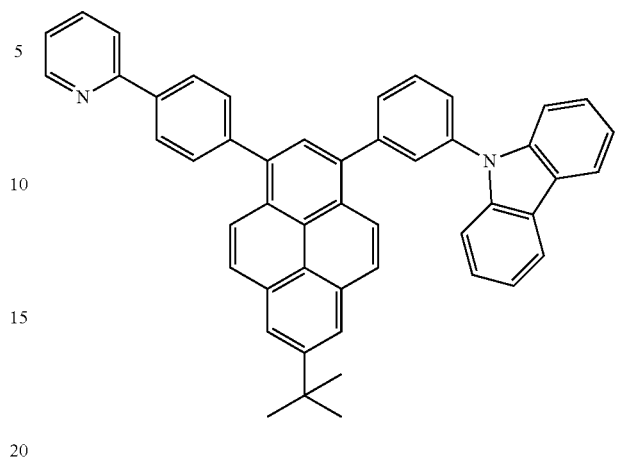
ET4
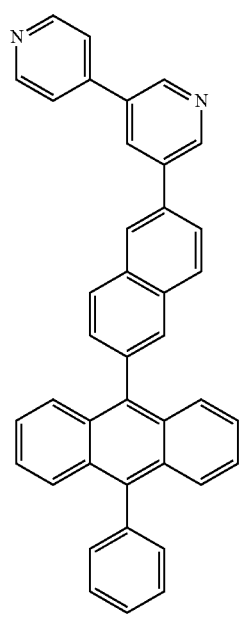
ET7
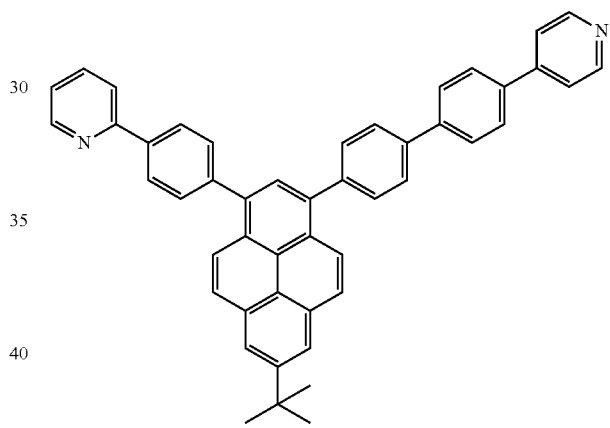
ET5
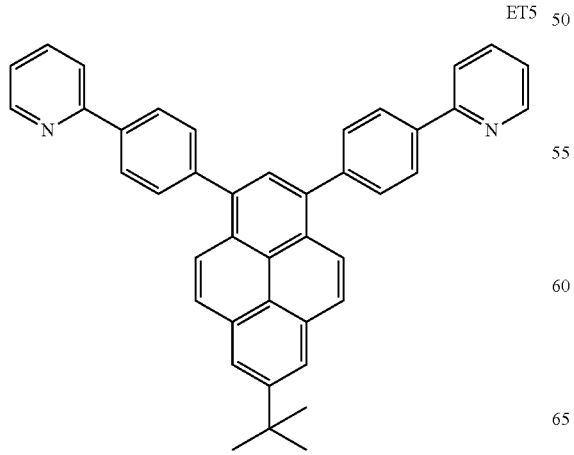
ET8
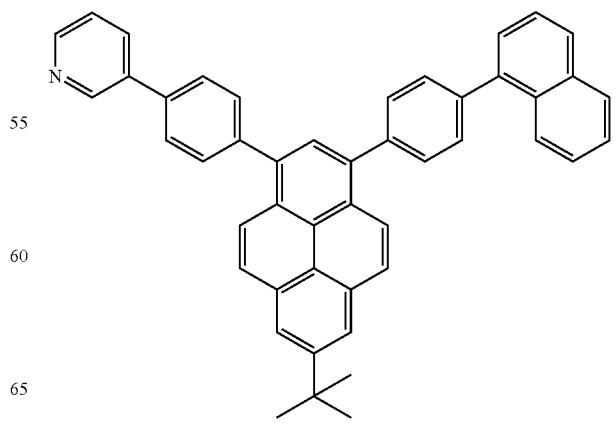

ET9
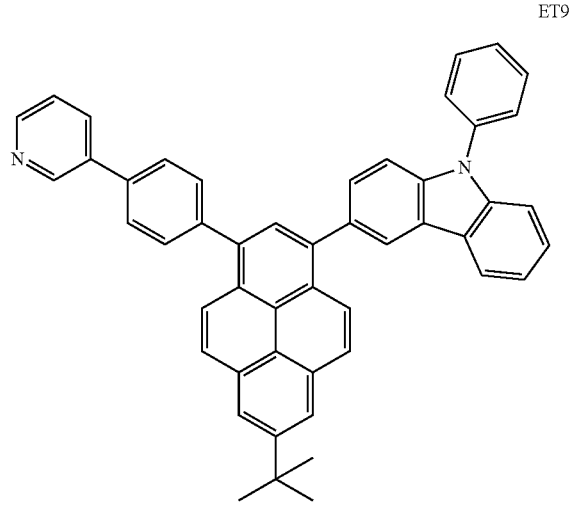
ET10
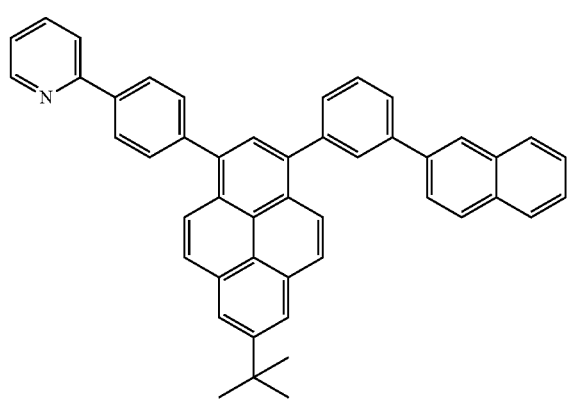
ET11
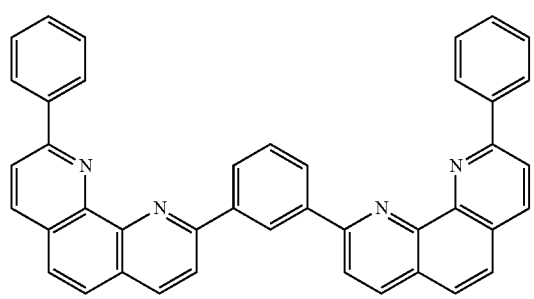
ET12
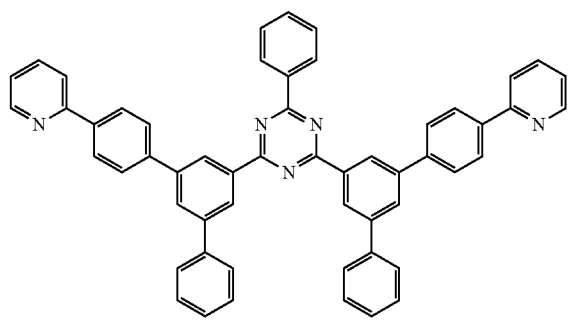
ET13
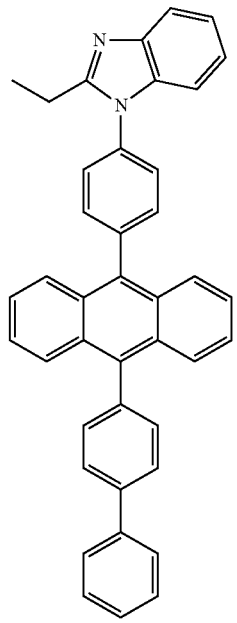
ET14
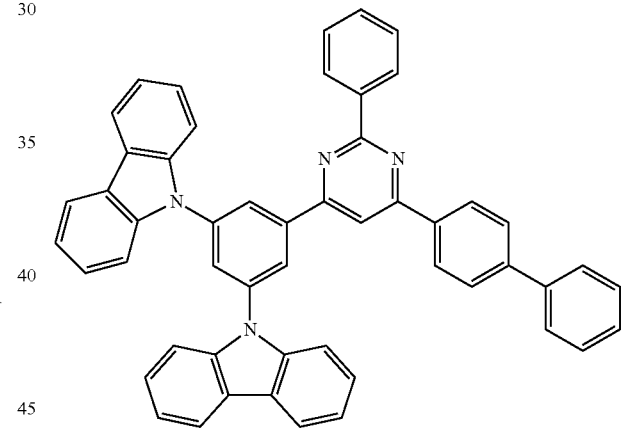
ET15
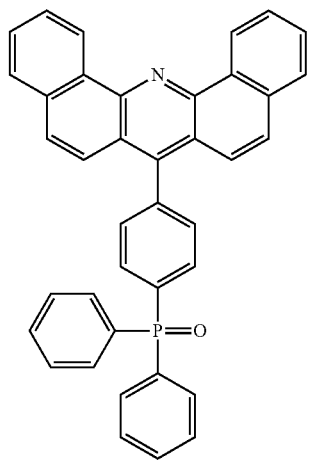

ET16

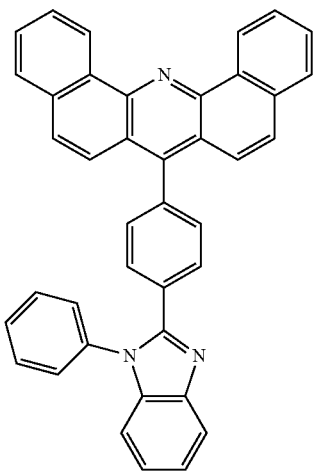

ET17

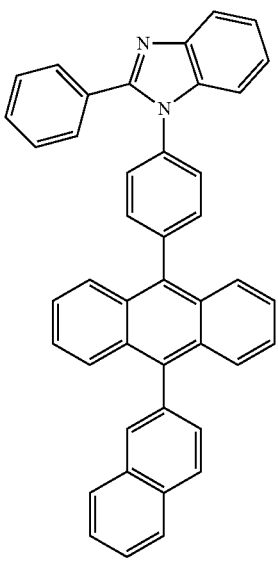

ET18

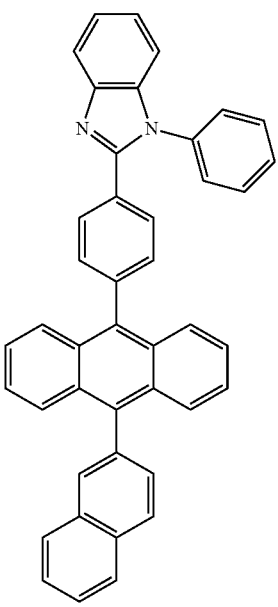

ET19

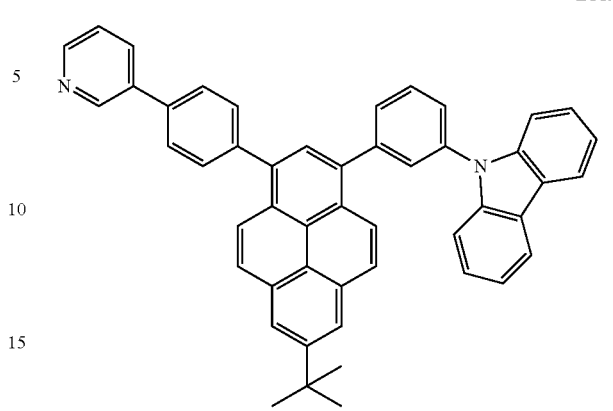

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

ET-D1

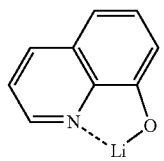

ET-D2

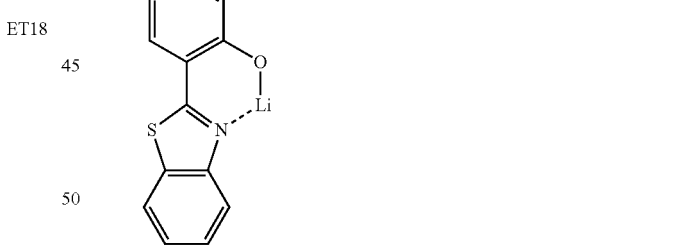

The electron transport region may include an electron injection layer (EIL) that allows electrons to be easily provided from a second electrode 19.

The electron injection layer may include at least one selected from, LiF, NaCl, CsF, $Li_2O$, BaO, and LiQ.

A thickness of the electron injection layer may be in a range of about 1 Å to about 100 Å, about 3 Å to about 90 Å. When the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as a material for forming the second electrode 19. To manufacture a top emission type light-emitting device, a transmissive electrode formed using ITO or IZO may be used as the second electrode 19.

Hereinbefore, the organic light-emitting device has been described with reference to FIG. 1, but is not limited thereto.

A $C_1$-$C_{60}$ alkyl group used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group used herein refers to a divalent group having the same structure as the $C_2$-$C_{60}$ alkenyl group.

A $C_2$-$C_{60}$ alkynyl group used herein refers to a hydrocarbon group formed by substituting at least one carbon trip bond in the middle or at the terminal of the $C_2$-$C_{60}$ alkyl group. Detailed examples thereof are an ethynyl group, and a propynyl group. A $C_2$-$C_{60}$ alkynylene group used herein refers to a divalent group having the same structure as the $C_2$-$C_{60}$ alkynyl group.

A $C_3$-$C_{10}$ cycloalkyl group used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_2$-$C_{10}$ heterocycloalkyl group used herein refers to a monovalent monocyclic group having at least one hetero atom selected from N, O, P, and S as a ring-forming atom and 2 to 10 carbon atoms. Detailed examples thereof are a tetrahydrofuranyl group, and a tetrahydrothiophenyl group. A $C_2$-$C_{10}$ heterocycloalkylene group used herein refers to a divalent group having the same structure as the $C_2$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromaticity. Detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_2$-$C_{10}$ heterocycloalkenyl group used herein refers to a monovalent monocyclic group that has at least one hetero atom selected from N, O, P, and S as a ring-forming atom, 2 to 10 carbon atoms, and at least one double bond in its ring. Detailed examples of the $C_2$-$C_{10}$ heterocycloalkenyl group are a 2,3-dihydrofuranyl group and a 2,3-dihydrothiophenyl group. A $C_2$-$C_{10}$ heterocycloalkenylene group used herein refers to a divalent group having the same structure as the $C_2$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_2$-$C_{60}$ heteroaryl group used herein refers to a monovalent group having a carbocyclic aromatic system that has at least one hetero atom selected from N, O, P, and S as a ring-forming atom, and 2 to 60 carbon atoms. A $C_2$-$C_{60}$ heteroarylene group used herein refers to a divalent group having a carbocyclic aromatic system that has at least one hetero atom selected from N, O, P, and S as a ring-forming atom, and 2 to 60 carbon atoms. Examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

A monovalent non-aromatic condensed polycyclic group used herein refers to a monovalent group (for example, having 8 to 60 carbon atoms) that has two or more rings condensed to each other, only carbon atoms as ring forming atoms, wherein the molecular structure as a whole is non-aromatic in the entire molecular structure. A detailed example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group (for example, having 2 to 60 carbon atoms) that has two or more rings condensed to each other, has a heteroatom selected from N, O P, and S, other than carbon atoms, as ring forming atoms, wherein the molecular structure as a whole is non-aromatic in the entire molecular structure. An example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

At least one of substituents of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

For example, at least one of substituents of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —N($Q_{11}$)($Q_{12}$), —Si($Q_{13}$)($Q_{14}$)($Q_{15}$), and —B($Q_{16}$)($Q_{17}$);

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$ and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that a molar equivalent of A was identical to a molar equivalent of B.

EXAMPLES

Synthesis Example 1

Synthesis of Intermediate A-1

Intermediate A-1 was synthesized as shown in Reaction Scheme 1.

Reaction Scheme 1

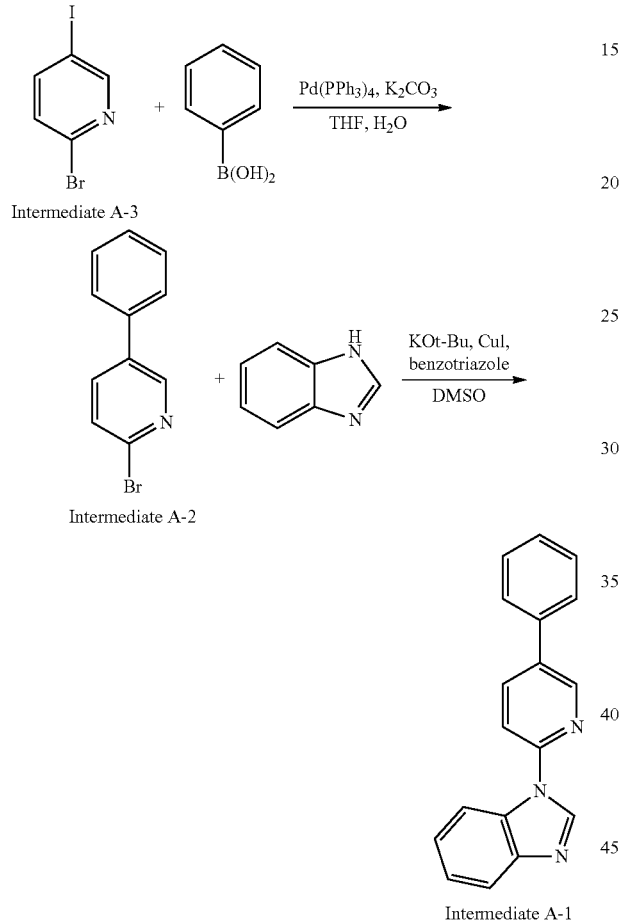

Intermediate A-1

Synthesis of Intermediate A-2

Intermediate A-3 (25 g), phenyl boronic acid (10.74 g), Pd(PPh$_3$)$_4$ (3.05 g), K$_2$CO$_3$ (24.3 g), and THF (333 mL), and distilled water (166 mL) were all placed in a 1 L reaction container, and then refluxed under nitrogen for 12 hours. When the reaction stopped, the result was cooled to room temperature, and then, an aqueous layer was removed, and an organic layer collected was washed once with 5% brine (500 mL) and once with distilled water (500 mL). The resultant organic layer was dried with MgSO$_4$, and then, a solvent was removed therefrom, and then, the result was refined by silica gel column chromatography using a mixed solvent including ethyl acetate (EA) and n-hexane (at a ratio of 3:97) solvent to obtain Intermediate A-2 (12.4 g).

LC-MS (m/z): 233.98 [M+1]

Synthesis of Intermediate A-1

Intermediate A-2 (10 g), benzimidazole (5 g), KOt-Bu (6.7 g), CuI (0.4 g), benzotriazole (0.5 g), and dimethylsulfoxide (50 mL) were all placed in a 100 mL reaction container, and then, refluxed under nitrogen for 12 hours. When the reaction stopped, the result was cooled to room temperature, and then, ethyl acetate (1 L) and 0.1 N HCl aqueous solution (1 L) were added thereto, and then, an organic layer was isolated and washed with 5% brine (1 L). The resultant organic layer was dried with MgSO$_4$, and then, a solvent was removed therefrom, and then, the result was refined by silica gel column chromatography using a mixed solvent including EA and n-hexane (at a ratio of 50:50) solvent to obtain Intermediate A-1 (4.98 g).

LC-MS (m/z): 272.21 [M+1]

Synthesis Example 2

Synthesis of Intermediate B-1

Synthesis of Intermediate B-2

Intermediate B-2 was synthesized in the same manner as used to synthesize Intermediate A-2 in Synthesis Example 1, except that Intermediate B-3 shown in Table 2 was used instead of Intermediate A-3. The synthesis yield and MS data of Intermediate B-2 are shown in Table 2.

Synthesis of Intermediate B-1

Intermediate B-1 was synthesized in the same manner as used to synthesize Intermediate A-1 in Synthesis Example 1, except that Intermediate B-2 was used instead of Intermediate A-2. The synthesis yield and MS data of Intermediate B-1 are shown in Table 2.

Synthesis Example 3

Synthesis of Intermediate C-1

Synthesis of Intermediate C-2

Intermediate C-2 was synthesized in the same manner as used to synthesize Intermediate A-2 in Synthesis Example 1, except that Intermediate C-3 shown in Table 2 was used instead of Intermediate A-3. The synthesis yield and MS data of Intermediate C-2 are shown in Table 2.

Synthesis of Intermediate C-1

Intermediate C-1 was synthesized in the same manner as used to synthesize Intermediate A-1 in Synthesis Example 1, except that Intermediate C-2 was used instead of Intermediate A-2. The synthesis yield and MS data of Intermediate C-1 are shown in Table 2.

Synthesis Example 4

Synthesis of Intermediate D-1

Intermediate D-1 was synthesized in the same manner as used to synthesize Intermediate A-1 in Synthesis Example 1, except that in synthesizing A-1, Intermediate D-2 was used instead of Intermediate A-2. The synthesis yield and MS data of Intermediate D-1 are shown in Table 2.

Synthesis Example 5

Synthesis of Compound 1

Compound 1 was synthesized as shown in Reaction Scheme 2.

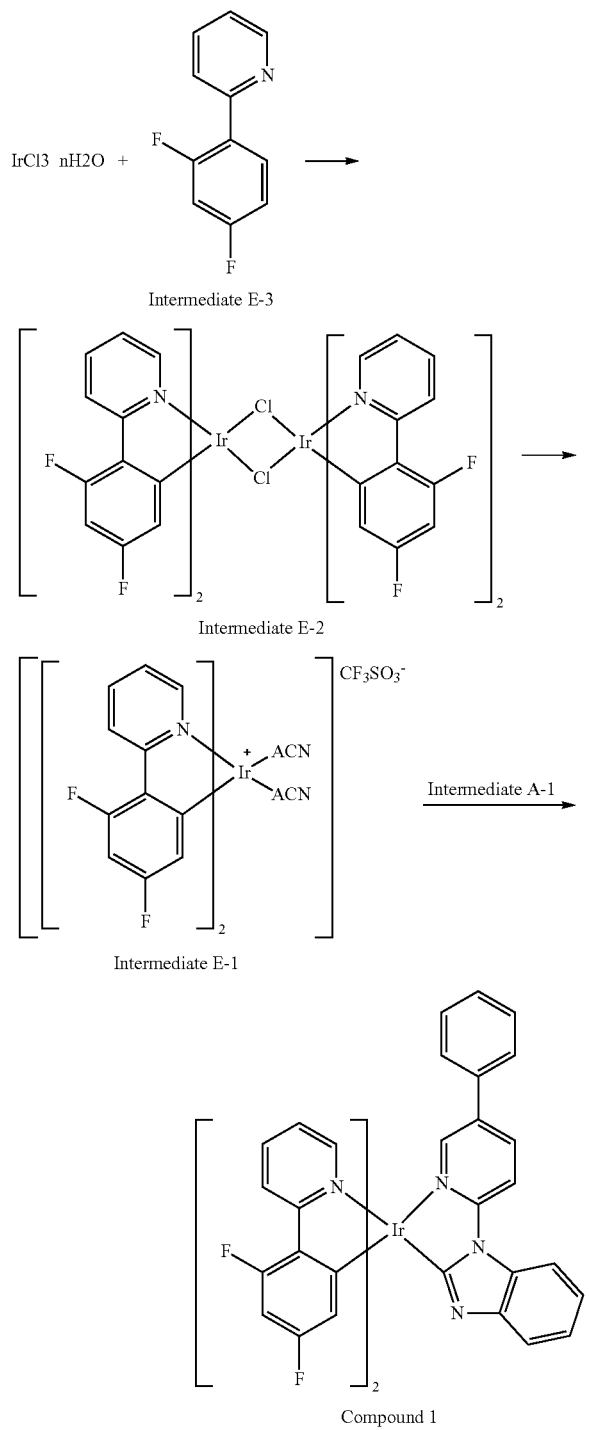

Reaction Scheme 2

Synthesis of Intermediate E-2

IrCl$_3$-nH$_2$O (18.7 g), E-3 (30 g), 2-ethoxyethanol (225 mL), and distilled water (75 mL) were all placed in a 1 L reaction container, and then, refluxed under nitrogen for 12 hours. When the reaction stopped, the result was cooled to room temperature. Then, distilled water (750 mL) was added to the reaction container and a solid produced was filtered, followed by being washed with distilled water (1 L), and then vacuum dried at a temperature of 60° C. for 12 hours to prepare Intermediate E-2 (23.7 g).

MALDI-TOF (m/z): 1216.05 [M]$^+$

Synthesis of Intermediate E-1

Intermediate E-2 (23 g), AgCF$_3$SO$_3$ (10.2 g), and acetonitrile (500 mL) were all placed in a 1 L reaction container, and then under nitrogen, refluxed for 12 hours. When the reaction stopped, the result was cooled to room temperature, and then, celite filtration was performed thereon to concentrate the residual filtrate, which was then vacuum dried for 12 hours to obtain Intermediate E-1 (27.3 g).

MALDI-TOF (m/z): 573.06 [M-2ACN,-Otf]$^+$

Synthesis of Compound 1

Intermediate E-1 (5 g), Intermediate A-1 (4.2 g), and 2-ethoxyethanol (150 mL) were all placed in a 500 mL reaction container, and then, under nitrogen, refluxed for 12 hours. When the reaction stopped, the result was cooled to room temperature, and then, distilled water (300 mL) was added thereto, and a solid produced was filtered, and washed with distilled water (200 mL). The resultant solid was dried and then refined by silica gel chromatography using a mixed solvent including dichloromethane and methanol (at a ratio of 90 to 10) to obtain Compound 1 (2.6 g).

MALDI-TOF (m/z): 843.16 [M]$^+$

Synthesis Example 6

Synthesis of Compound 2

Compound 2 was synthesized in the same manner as in Synthesis Example 5, except that in synthesizing Compound 1, Intermediate B-1 shown in Table 2 was used instead of Intermediate A-1. The synthesis yield and MS data of Compound 2 are shown in Table 2.

Synthesis Example 7

Synthesis of Compound 3

Compound 3 was synthesized in the same manner as in Synthesis Example 5, except that in synthesizing Compound 1, Intermediate C-1 shown in Table 2 was used instead of Intermediate A-1. The synthesis yield and MS data of Compound 3 are shown in Table 2.

Synthesis Example 8

Synthesis of Compound 4

Compound 4 was synthesized in the same manner as in Synthesis Example 5, except that in synthesizing Compound 1, Intermediate D-1 shown in Table 2 was used instead of Intermediate A-1. The synthesis yield and MS data of Compound 4 are shown in Table 3.

Synthesis Example 9

Synthesis of Compound 5

Compound 5 was synthesized in the same manner as in Synthesis Example 5, except that Intermediate F-3 shown in Table 2 was used instead of Intermediate E-3. The synthesis yield and MS data of Compound 5 are shown in Table 2.

Synthesis Example 10

Synthesis of Compound 6

Compound 6 was synthesized in the same manner as in Synthesis Example 5, except that Intermediate G-3 shown in Table 2 was used instead of Intermediate E-3. The synthesis yield and MS data of Compound 6 are shown in Table 2.

Synthesis Example 11

Synthesis of Compound 7

Compound 7 was synthesized as shown in Reaction Scheme 3.

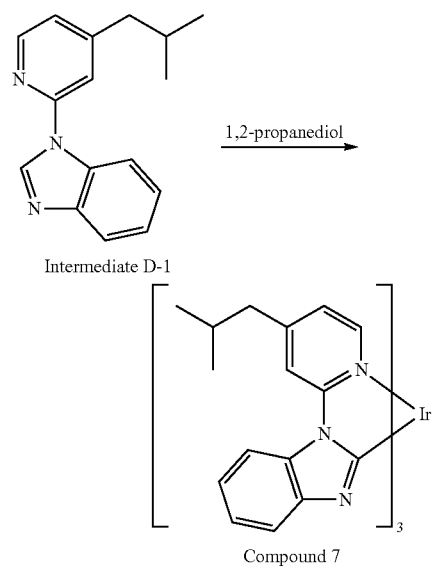

$Ir(COD)_2BF_4$ (4.0 g), Intermediate D-1 (10.14 g), and 1,2-propanediol (150 mL) were all placed in a 500 mL reaction container, and then, under nitrogen, refluxed for 12 hours. When the reaction stopped, the result was cooled to room temperature, and then, distilled water (300 mL) was added thereto, and a solid produced was filtered, and washed with distilled water (1 L). The resultant solid was dried, and then refined by silica gel chromatography using a mixed solvent including dichloromethane and methanol (at a ratio of 90 to 10) to obtain Compound 7 (2.4 g).

MALDI-TOF (m/z): 943.37 $[M]^+$

TABLE 2

| Reactant | Product | Yield of product (%) | MS (m/z) of product |
|---|---|---|---|
| A-3 | A-2 | 60 | 233.98 |

TABLE 2-continued
| Reactant | Product | Yield of product (%) | MS (m/z) of product |
|---|---|---|---|
| 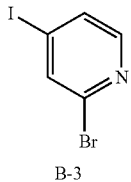 B-3 | 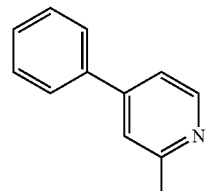 B-2 | 66 | 233.98 |
| 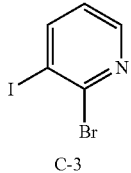 C-3 | 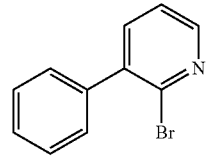 C-2 | 56 | 233.98 |
| 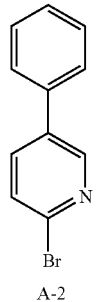 A-2 | 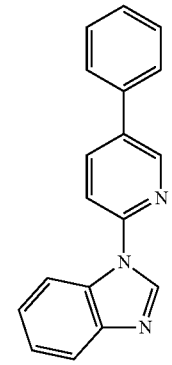 A-1 | 43 | 272.11 |
| 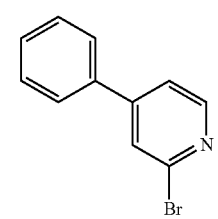 B-2 | 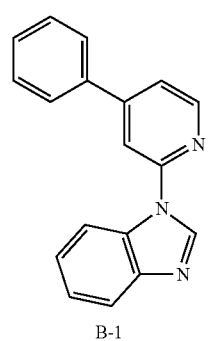 B-1 | 36 | 272.11 |
| 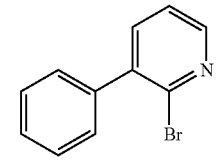 C-2 | 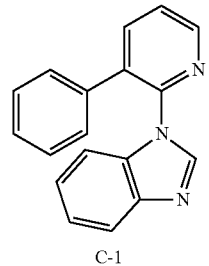 C-1 | 25 | 272.11 |

TABLE 2-continued
| Reactant | Product | Yield of product (%) | MS (m/z) of product |
|---|---|---|---|
| 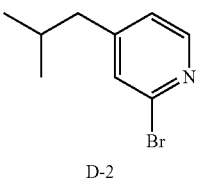 D-2 | 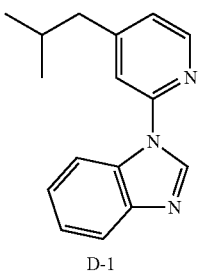 D-1 | 56 | 252.14 |
| 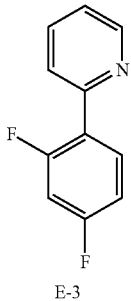 [SMILES: Fc1ccc(-c2ccccn2)c(F)c1] E-3 | 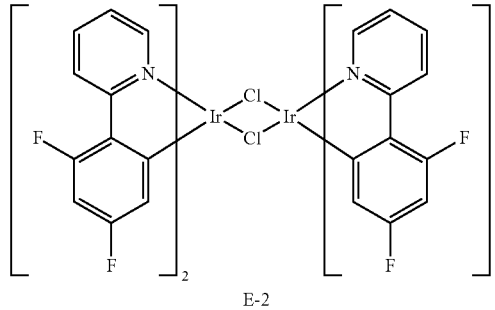 E-2 | 62 | 1216.05 |
| 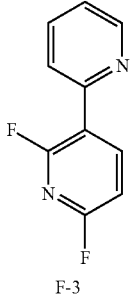 F-3 | 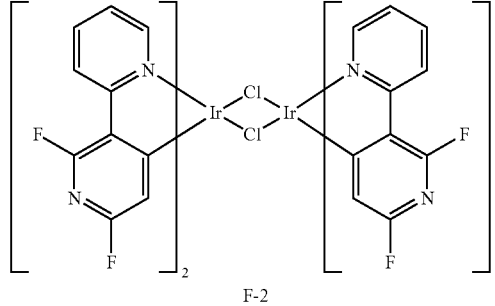 F-2 | 72 | 1220.03 |
| 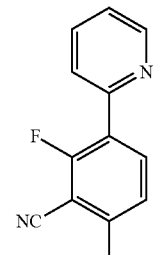 G-3 | 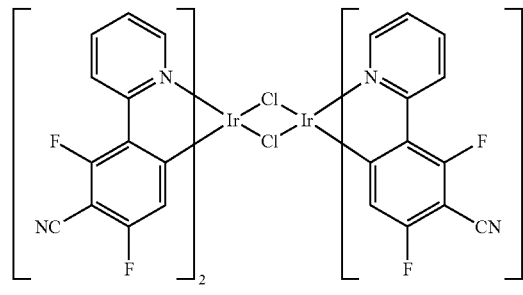 G-2 | 52 | 1316.03 |

TABLE 2-continued
| Reactant | Product | Yield of product (%) | MS (m/z) of product |
|---|---|---|---|
| 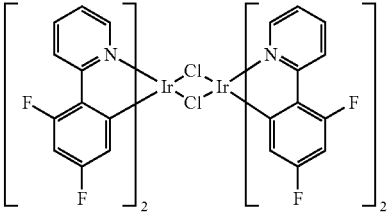 E-2 | 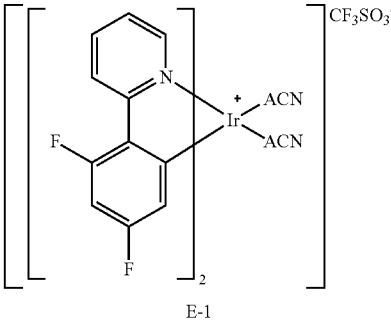 E-1 | 89 | 573.06 |
| 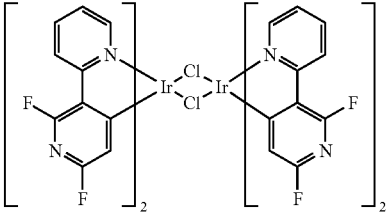 F-2 | 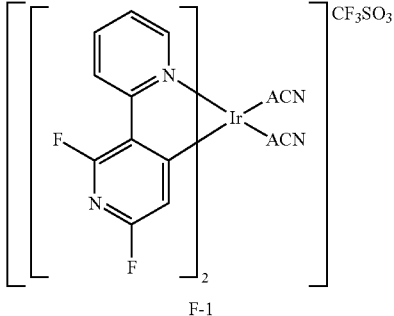 F-1 | 85 | 575.05 |
| 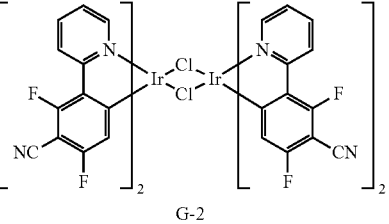 G-2 | 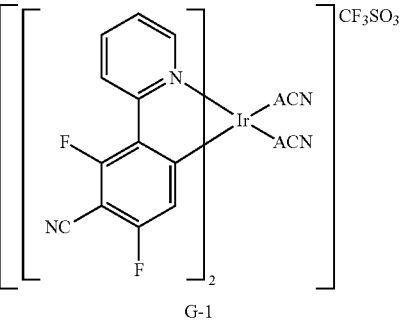 G-1 | 83 | 623.05 |
| E1 + A1 | 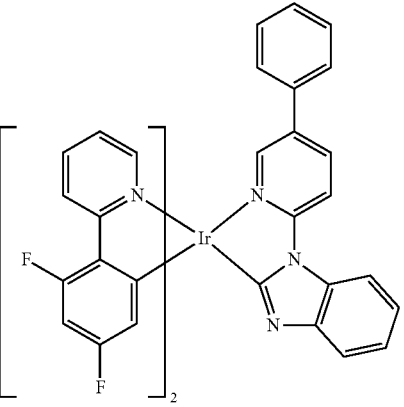 Compound 1 | 50 | 843.16 |

TABLE 2-continued
| Reactant | Product | Yield of product (%) | MS (m/z) of product |
|---|---|---|---|
| E1 + B1 | 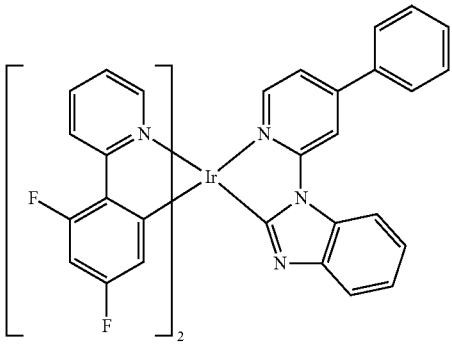<br>Compound 2 | 48 | 843.16 |
| E1 + C1 | 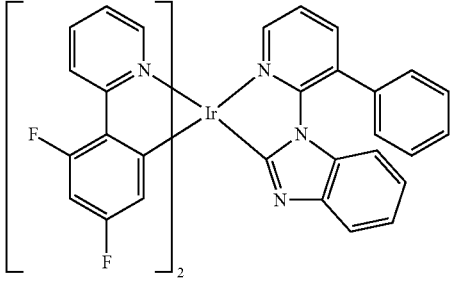<br>Compound 3 | 38 | 843.16 |
| E1 + D1 | 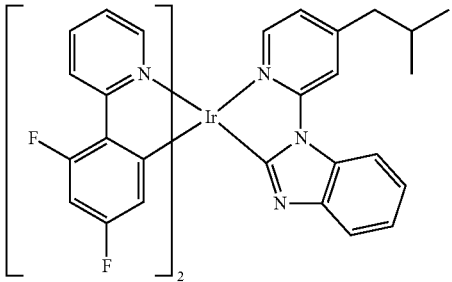<br>Compound 4 | 56 | 823.19 |
| F1 + A1 | 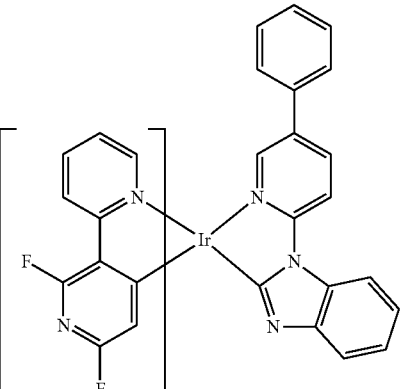<br>Compound 5 | 33 | 845.15 |

TABLE 2-continued

| Reactant | Product | Yield of product (%) | MS (m/z) of product |
|---|---|---|---|
| G1 + A1 | 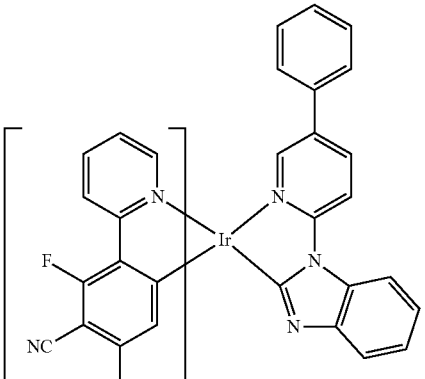  Compound 6 | 49 | 893.15 |
| D-1 | 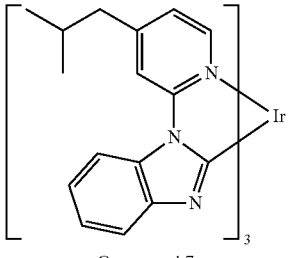  Compound 7 | 32 | 943.37 |

Evaluation Example 1

Photoluminescence (PL) Spectrum and Color Purity Evaluation

Compound 1 was diluted at a concentration of 10 mM in toluene, and PL of Compound 1 in solution was measured by using an ISC PC1 spectrofluorometer equipped with a xenon lamp. This experiment was performed on Compounds 2 to 7, and PL spectra of Compounds 1 to 7 were evaluated and results thereof are shown in Table 3.

PMMA in $CH_2Cl_2$ solution and 8 percent by weight (wt %) of Compound 1 were mixed, and the obtained mixture was coated on a quartz substrate by using a spin coater, and then heat treated in an oven at a temperature of 80° C., and cooled to room temperature to obtain a film. Color-coordination-in-film of Compound 1 was evaluated using a Hamamatsu photonics absolute PL quantum yield measurement system that is equipped with a xenon light source, a monochromator, a photonic multichannel analyzer, and an integrating sphere, and uses PLQY measurement software (Hamamatsu Photonics, Ltd., Shizuoka, Japan). This experiment was performed on Compounds 2 to 7, and results thereof are shown in Table 3.

TABLE 3

| Compound No. | $1^{st}$ & $2^{nd}$ $PL_{max}$ (nm) | $CIE_{x, y}$ | Half width (nm) |
|---|---|---|---|
| 1 | 458, 481 | (0.15, 0.25) | 70 |
| 2 | 454, 480 | (0.15, 0.23) | 64 |
| 3 | 452, 480 | (0.15, 0.22) | 62 |
| 4 | 452, 477 | (0.14, 0.20) | 70 |
| 5 | 441, 469 | (0.15, 0.15) | 61 |
| 6 | 444, 471 | (0.15, 0.18) | 70 |
| 7 | 467 | (0.18, 0.23) | 119 |

From Table 3, it was confirmed that Compounds 1 to 7 have excellent luminescent characteristics.

Evaluation Example 2

Evaluation on HOMO, LUMO, and Triplets (T1) Energy Levels of Synthesized Compounds HOMO, LUMO and T1 energy levels of Compounds 1 to 7 were evaluated according to the method indicated in Table 4, and results thereof are shown in Table 5.

TABLE 4

| | |
|---|---|
| HOMO energy level evaluation method | Each compound was diluted at a concentration of $1 \times 10^{-5}$M in $CHCl_3$, and an UV absorption spectrum thereof was measured at room temperature by using a Shimadzu UV-350 spectrometer, and a HOMO energy level thereof was calculated by using an optical band gap (Eg) from an edge of the absorption spectrum. |
| LUMO energy level evaluation method | A potential (V)-current (A) graph of each compound was obtained by using cyclic voltammetry (CV) (electrolyte: 0.1M $Bu_4NClO_4$/solvent: $CH_2Cl_2$/electrode: 3 electrode system (working electrode: GC, reference electrode: Ag/AgCl, auxiliary electrode: Pt)), and then, from reduction onset of the graph, a LUMO energy level of the compound was calculated. |
| T1 energy level evaluation method | A mixture (each compound was dissolved in an amount of 1 mg in 3 cc of toluene) of toluene and each compound was loaded into a quartz cell, and then, the resultant quartz cell was loaded into liquid nitrogen (77K) and a photoluminescence spectrum thereof was measured by using a device for measuring photoluminescence, and the obtained spectrum was compared with a photoluminescence spectrum measured at room temperature, and peaks observed only at low temperature were analyzed to calculate T1 energy levels. |

TABLE 5

| Compound No. | HOMO (eV) (calc.) | LUMO (eV) (calc.) | T1 energy level (eV) |
|---|---|---|---|
| 1 | −5.94 | −2.97 | 2.71 |
| 2 | −5.92 | −3.15 | 2.73 |
| 3 | −5.93 | −3.05 | 2.71 |
| 4 | −5.92 | −2.84 | 2.73 |
| 5 | −6.05 | −2.95 | 2.81 |
| 6 | −6.11 | −3.02 | 2.80 |
| 7 | −5.93 | −2.82 | 2.70 |

From Table 5, it was confirmed that Compounds 1 to 7 have electric characteristics that are suitable for use as a material for forming an organic light-emitting device.

Evaluation Example 3

Thermal Characteristics Evaluation of Synthesized Compounds

Each of Compounds 1 to 7 was subjected to thermal analysis ($N_2$ atmosphere, temperature range: room temperature to 800° C. (10° C./min)-TGA, room temperature to 400° C.-DSC, Pan Type: Pt Pan in disposable Al Pan(TGA), disposable Al pan(DSC)) using thermo gravimetric analysis (TGA) and differential scanning calorimetry (DSC), and obtained results are shown in Table 6 below. As shown in Table 6, it was confirmed that the synthesized compounds had excellent thermal stability.

TABLE 6

| Compound No. | Td (1%) (° C.) |
|---|---|
| 1 | 364 |
| 2 | 369 |
| 3 | 362 |
| 4 | 351 |
| 5 | 366 |
| 6 | 362 |
| 7 | 363 |

Example 1

A glass substrate with a 1,500 Å-thick ITO (indium tin oxide) electrode (first electrode, anode) formed thereon was washed with distilled water and sonicated with ultrasonic waves. When the washing with distilled water was completed, sonication washing was performed using a solvent, such as isopropyl alcohol, acetone, or methanol. The result was dried and then transferred to a plasma washer, and the resultant substrate was washed with oxygen plasma for 5 minutes and then, transferred to a vacuum depositing device.

Compound HT3 was vacuum deposited on the ITO electrode on the glass substrate to form a first hole injection layer having a thickness of 3,500 Å, and then, Compound HT-D1 was vacuum deposited on the first hole injection layer to form a second hole injection layer having a thickness of 300 Å, and TAPC was vacuum deposited on the second hole injection layer to form an electron blocking layer having a thickness of 100 Å, thereby completing the formation of a hole transport region.

mCP (host) and Compound 1 (dopant, 7 wt %) were co-deposited on the hole transport region to form an emission layer having a thickness of 300 Å.

Compound ET3 was vacuum deposited on the emission layer to form an electron transport layer having a thickness of 250 Å, and then, ET-D1 (Liq) was deposited on the electron transport layer to form an electron injection layer having a thickness of 5 Å, and an Al second electrode (cathode) having a thickness of 1,000 Å was formed on the electron injection layer, thereby completing manufacturing of an organic light-emitting device.

Example 2

An organic light-emitting device was manufactured in the same manner as in Example 1, except that in forming an emission layer, as a dopant, Compound 2 was used instead of Compound 1.

Example 3

An organic light-emitting device was manufactured in the same manner as in Example 1, except that in forming an emission layer, as a dopant, Compound 3 was used instead of Compound 1.

Example 4

An organic light-emitting device was manufactured in the same manner as in Example 1, except that in forming an emission layer, as a dopant, Compound 4 was used instead of Compound 1.

Example 5

An organic light-emitting device was manufactured in the same manner as in Example 1, except that in forming an emission layer, as a dopant, Compound 5 was used instead of Compound 1.

Example 6

An organic light-emitting device was manufactured in the same manner as in Example 1, except that in forming an emission layer, as a dopant, Compound 6 was used instead of Compound 1.

Example 7

An organic light-emitting device was manufactured in the same manner as in Example 1, except that in forming an emission layer, as a dopant, Compound 7 was used instead of Compound 1.

Comparative Example 1

An organic light-emitting device was manufactured in the same manner as in Example 1, except that in forming an emission layer, as a dopant, Compound A was used instead of Compound 1.

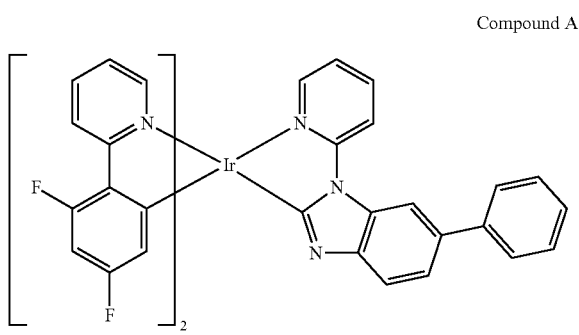

Compound A

Comparative Example 2

An organic light-emitting device was manufactured in the same manner as in Example 1, except that in forming an emission layer, as a dopant, Compound B was used instead of Compound 1.

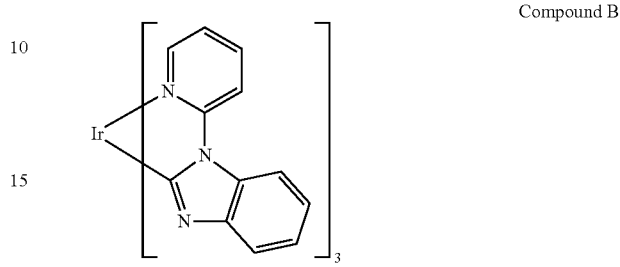

Compound B

Evaluation Example 4

Evaluation on Characteristics of an Organic Light-Emitting Device

The current density, brightness, and luminescence efficiency, and half-lifespan according to voltage of the organic light-emitting devices manufactured according to Examples 1 to 7, and Comparative Examples 1 and 2 were measured, the measurement method is described in detail below, and results thereof are shown in Table 7. $T_{80}$ lifespan indicates a period of time (hr) taken for the brightness to reach 80% with respect to 100% of initial brightness:

(1) Change in Current Density According to Voltage

Regarding the manufactured organic light-emitting device, a current flowing in a unit device was measured by using a current-voltage meter (Keithley 2400) while a voltage was raised from 0 volts (V) to 10 V, and the measured current value was divided by an area.

(2) Change in Brightness According to Voltage

Regarding the manufactured organic light-emitting device, brightness was measured by using Minolta Cs-1000A while a voltage was raised from 0 V to 10 V.

(3) Luminescence Efficiency Measurement

Current efficiency (candelas per ampere, cd/A) was measured at the same current density (10 milliamperes per square centimeter, $mA/cm^2$) by using brightness, current density, and voltage measured according to (1) and (2).

TABLE 7

| | Host | Dopant | Driving Voltage (V) | Current efficiency (cd/A) | Brightness (cd/m²) | $T_{80}$ Lifespan (hr) | Color coordinate CIE x | CIE y |
|---|---|---|---|---|---|---|---|---|
| Example 1 | mCP | Compound 1 | 6.2 | 16.3 | 500 | 8.2 | 0.15 | 0.24 |
| Example 2 | mCP | Compound 2 | 6.4 | 18.2 | 500 | 7.1 | 0.15 | 0.22 |
| Example 3 | mCP | Compound 3 | 6.1 | 15.4 | 500 | 10.1 | 0.15 | 0.21 |
| Example 4 | mCP | Compound 4 | 6.6 | 13.7 | 500 | 3.2 | 0.15 | 0.20 |
| Example 5 | mCP | Compound 5 | 6.5 | 10.6 | 500 | 1.2 | 0.14 | 0.15 |
| Example 6 | mCP | Compound 6 | 6.6 | 11.9 | 500 | 2.8 | 0.15 | 0.17 |
| Example 7 | mCP | Compound 7 | 6.5 | 13.9 | 500 | 5.6 | 0.16 | 0.24 |
| Comparative Example 1 | mCP | Compound A | 6.8 | 10.4 | 500 | 0.7 | 0.15 | 0.21 |
| Comparative Example 2 | mCP | Compound B | 6.6 | 12.1 | 500 | 0.3 | 0.17 | 0.26 |

From Table 7, it was confirmed that the organic light-emitting devices of Examples 1 to 7 had, compared to the organic light-emitting devices of Comparative Examples 1 and 2, similar color purity, low driving voltage, high current density, high brightness, and long lifespan. Although not limited to a particular theory, as shown in Table 7, the organic light-emitting devices of Examples 1 to 7 have substantially prolonged lifespan characteristics compared to the organic light-emitting devices of Comparative Examples 1 and 2. While not wanting to be bound by a theory, it is understood that when each of $R_5$ to $R_8$ in Formula 2 is not simultaneously a hydrogen (that is, $R_5$ to $R_8$ in Formula 2 include at least one substituent that is not a hydrogen), stability of a pyridine ring of Formula 2 associated with a LUMO level of the organometallic compound described above Formula 1 improves.

The organometallic compound according to embodiments has excellent electric characteristics and thermal stability. Accordingly, an organic light-emitting device including the organometallic compound may have a low driving voltage, high efficiency, high brightness, and a long lifespan.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present inventive concept as defined by the following claims.

What is claimed is:

1. An organic light-emitting device comprising:
   a first electrode;
   a second electrode; and
   an organic layer disposed between the first electrode and the second electrode,
   wherein the organic layer comprises an emission layer, and further comprises at least one organometallic compound represented by Formula 1:

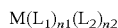   Formula 1 wherein in Formula 1,
   M is Ir;
   $L_1$ is selected from ligands represented by Formulae 2A, 2C, and 2D;
   $L_2$ is selected from ligands represented by Formulae 3-1 and 3-2, and is different from $L_1$;
   n1 is 1, 2, or 3;
   n2 is 0, 1, or 2;
   when n1 is two or more, ligands $L_1$ are identical or different, and when n2 is two or more, $L_2$ are identical or different;

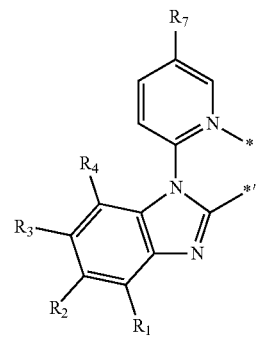

Formula 2A

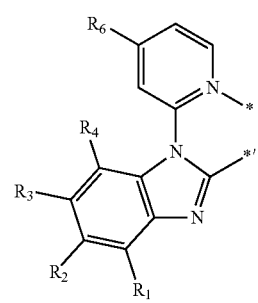

Formula 2C

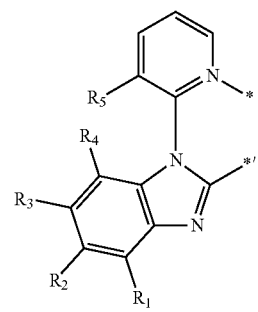

Formula 2D wherein in Formulae 2A, 2C, and 2D,
$R_1$ to $R_4$ are each hydrogen,
$R_5$ to $R_7$ are each independently selected from an isobutyl group and a phenyl group; and
*and*' each indicates a binding site to M in Formula 1;

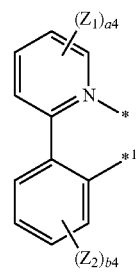

Formula 3-1

-continued

Formula 3-2

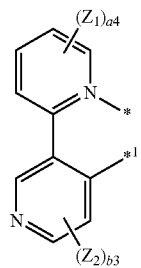

Formula 4

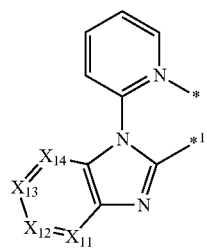

wherein in Formulae 3-1 and 3-2, $Z_1$ is hydrogen, $Z_2$ is —F, a4 is 4;

b4 is 2;

b3 is 2;

and

\*and\*¹ each indicates a binding site to M in Formula 1.

2. The organic light-emitting device of claim 1, wherein the first electrode is an anode, the second electrode is a cathode, and the organic layer comprises i) a hole transport region disposed between the first electrode and the emission layer, wherein the hole transport region comprises at least one of a hole injection layer, a hole transport layer, and an electron blocking layer, and ii) an electron transport region disposed between the emission layer and the second electrode, wherein the electron transport region comprises at least one selected from a hole blocking layer, an electron transport layer, and an electron injection layer.

3. The organic light-emitting device of claim 2, wherein the emission layer comprises the organometallic compound of claim 1 and a host, wherein an amount of the organometallic compound in the emission layer is smaller than an amount of the host.

4. An organic light-emitting device comprising:

a first electrode;

a second electrode; and an organic layer disposed between the first electrode and the second electrode wherein the organometallic compound is one of Compounds 1 to 7:

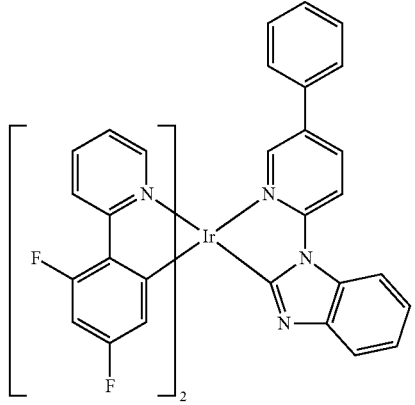

1

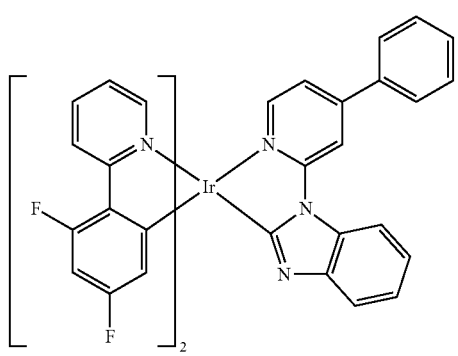

2

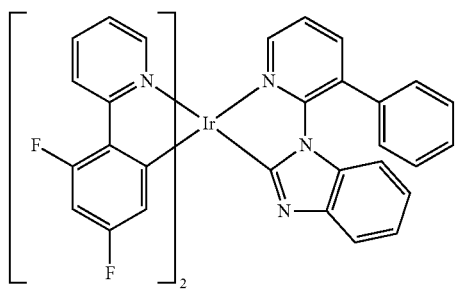

3

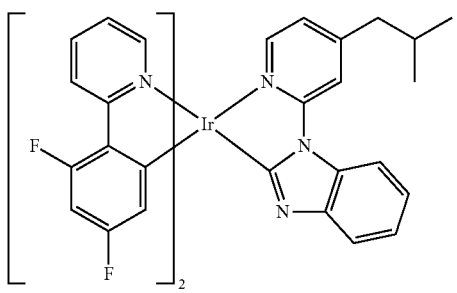
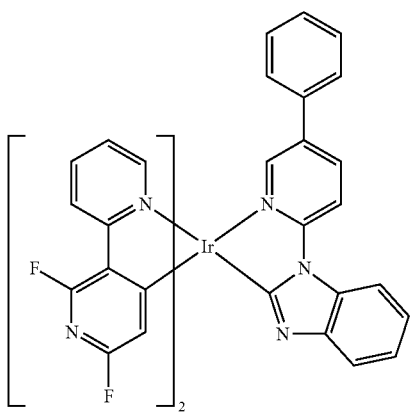
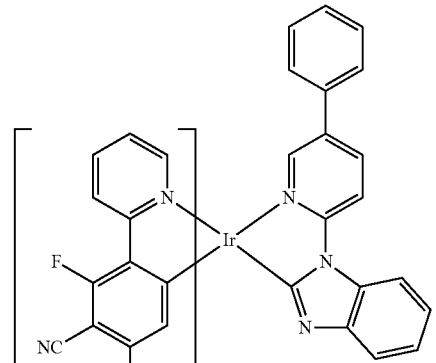
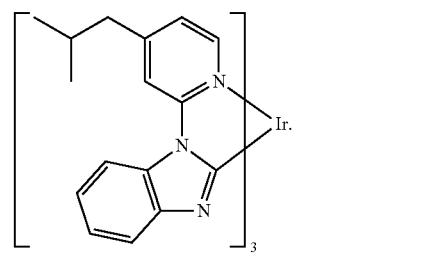
* * * * *